(12) United States Patent
Tantawi et al.

(10) Patent No.: US 10,485,991 B2
(45) Date of Patent: Nov. 26, 2019

(54) METHODS AND SYSTEMS FOR RF POWER GENERATION AND DISTRIBUTION TO FACILITATE RAPID RADIATION THERAPIES

(71) Applicant: THE BOARD OF TRUSTEES OF THE LELAND STANFORD JUNIOR UNIVERSITY, Palo Alto, CA (US)

(72) Inventors: Sami Tantawi, Stanford, CA (US); Valery A. Dolgashev, San Carlos, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 586 days.

(21) Appl. No.: 15/068,268

(22) Filed: Mar. 11, 2016

(65) Prior Publication Data
US 2016/0193481 A1 Jul. 7, 2016

Related U.S. Application Data

(63) Continuation of application No. PCT/US2014/055260, filed on Sep. 11, 2014.
(Continued)

(51) Int. Cl.
*A61N 5/10* (2006.01)
*H05H 7/02* (2006.01)
(Continued)

(52) U.S. Cl.
CPC ......... *A61N 5/1048* (2013.01); *A61N 5/1039* (2013.01); *A61N 5/1077* (2013.01);
(Continued)

(58) Field of Classification Search
USPC .................................. 315/500–505
See application file for complete search history.

(56) References Cited

U.S. PATENT DOCUMENTS

| 3,757,118 A | 9/1973 | Hodge et al. |
| 4,644,168 A | 2/1987 | Rand et al. |

(Continued)

FOREIGN PATENT DOCUMENTS

| CN | 101453951 | 6/2009 |
| CN | 104246961 | 12/2014 |

(Continued)

OTHER PUBLICATIONS

Brahme et al., "Electron and Photon Beams from a 50 MeV Racetrack Microtron", Acta Oncologica. vol. 19. No. 4, Jan. 1, 1980, pp. 305-319.
(Continued)

*Primary Examiner* — Dion Ferguson
*Assistant Examiner* — Srinivas Sathiraju
(74) *Attorney, Agent, or Firm* — Kilpatrick Townsend & Stockton LLP

(57) ABSTRACT

Methods and system for facilitating rapid radiation treatments are provided herein and relate in particular to radiation generation and delivery, power production and distribution, and electron source design. The methods and systems described herein are particularly advantageous when used with a compact high-gradient, very high energy electron (VHEE) accelerator and delivery system (and related processes) capable of treating patients from multiple beam directions with great speed, using all-electromagnetic or radiofrequency deflection steering is provided, that can deliver an entire dose or fraction of high-dose radiation
(Continued)

therapy sufficiently fast to freeze physiologic motion, yet with a better degree of dose conformity or sculpting than conventional photon therapy.

23 Claims, 19 Drawing Sheets

Related U.S. Application Data

(60) Provisional application No. 62/022,469, filed on Jul. 9, 2014, provisional application No. 62/003,002, filed on May 26, 2014, provisional application No. 61/876,679, filed on Sep. 11, 2013.

(51) Int. Cl.
  *H05H 9/04* (2006.01)
  *G05B 15/02* (2006.01)
  *G05F 1/66* (2006.01)

(52) U.S. Cl.
  CPC ......... *A61N 5/1081* (2013.01); *A61N 5/1084* (2013.01); *G05B 15/02* (2013.01); *G05F 1/66* (2013.01); *H05H 7/02* (2013.01); *H05H 9/04* (2013.01); *A61N 2005/1034* (2013.01); *A61N 2005/1054* (2013.01); *A61N 2005/1074* (2013.01); *A61N 2005/1089* (2013.01); *H05H 2007/025* (2013.01)

(56) References Cited

U.S. PATENT DOCUMENTS

| | | | |
|---|---|---|---|
| 4,726,046 A | 2/1988 | Nunan et al. | |
| 4,737,647 A | 4/1988 | Stieber | |
| 4,827,491 A | 5/1989 | Barish | |
| 5,452,720 A | 9/1995 | Smith et al. | |
| 5,661,377 A * | 8/1997 | Mishin | H05H 7/02 315/5.41 |
| 5,684,854 A | 11/1997 | Hughes | |
| 5,729,584 A | 3/1998 | Moorman et al. | |
| 5,847,401 A | 12/1998 | Davies et al. | |
| 5,859,893 A | 1/1999 | Moorman et al. | |
| 6,332,017 B1 | 12/2001 | Carroll et al. | |
| 6,333,966 B1 | 12/2001 | Schoen | |
| 6,353,227 B1 | 3/2002 | Boxen | |
| 6,459,762 B1 | 10/2002 | Wong et al. | |
| 6,463,123 B1 * | 10/2002 | Korenev | G21K 5/10 378/119 |
| 6,537,052 B1 | 3/2003 | Adler | |
| 6,559,610 B2 | 5/2003 | Tanaka | |
| 6,628,750 B1 * | 9/2003 | Korenev | G21K 5/04 250/453.11 |
| 6,714,620 B2 | 3/2004 | Caflisch et al. | |
| 6,724,782 B2 | 4/2004 | Hartemann et al. | |
| 6,728,335 B1 | 4/2004 | Thomson et al. | |
| 6,768,265 B1 * | 7/2004 | Ives | H01J 23/065 315/5.16 |
| 6,794,656 B2 * | 9/2004 | Francke | G01T 1/2935 250/336.1 |
| 6,847,168 B1 * | 1/2005 | Ives | H01J 25/10 315/5.14 |
| 6,937,693 B2 | 8/2005 | Svatos | |
| 6,977,987 B2 | 12/2005 | Yamashita et al. | |
| 7,085,347 B2 | 8/2006 | Mihara et al. | |
| 7,164,748 B2 * | 1/2007 | Francke | A61B 6/02 378/196 |
| 7,167,540 B2 | 1/2007 | Muller et al. | |
| 7,180,243 B2 | 2/2007 | Secheresse et al. | |
| 7,190,764 B2 | 3/2007 | Mori et al. | |
| 7,206,379 B2 | 4/2007 | Lemaitre | |
| 7,385,354 B2 * | 6/2008 | Miyake | H01J 23/087 250/396 R |
| 7,391,850 B2 | 6/2008 | Kaertner et al. | |
| 7,486,775 B2 | 2/2009 | Forster et al. | |
| 7,601,966 B2 * | 10/2009 | Ben-Haim | G01T 1/1648 250/394 |
| 7,630,474 B2 | 12/2009 | Clayton | |
| 7,741,624 B1 | 6/2010 | Sahadevan | |
| 7,816,870 B2 * | 10/2010 | Yakovlev | H05H 7/22 315/5.39 |
| 7,835,492 B1 | 11/2010 | Sahadevan | |
| 7,838,838 B2 * | 11/2010 | Rousso | G01T 1/1648 250/394 |
| 7,839,972 B2 | 11/2010 | Ruchala et al. | |
| 8,027,431 B2 | 9/2011 | Stahl et al. | |
| 8,039,819 B2 | 10/2011 | Faure et al. | |
| 8,173,983 B1 | 5/2012 | Sahadevan | |
| 8,232,748 B2 * | 7/2012 | Treas | H05H 7/02 250/390.1 |
| 8,315,357 B2 | 11/2012 | Zhu et al. | |
| 8,350,226 B2 | 1/2013 | Zdasiuk et al. | |
| 8,405,044 B2 | 3/2013 | MacKinnon et al. | |
| 8,547,006 B1 * | 10/2013 | Ives | H01J 25/10 313/383 |
| 8,575,579 B2 | 11/2013 | Moskvin et al. | |
| 8,610,075 B2 * | 12/2013 | Rousso | A61K 51/0478 250/362 |
| 8,618,521 B2 * | 12/2013 | Loo | A61N 5/1065 250/492.1 |
| 8,624,496 B2 * | 1/2014 | Neubauer | H01J 25/587 315/39.51 |
| 8,674,630 B1 * | 3/2014 | Cornelius | H05H 7/20 315/5.41 |
| 8,787,529 B2 * | 7/2014 | Graves | H05G 2/00 250/493.1 |
| 9,018,603 B2 * | 4/2015 | Loo | A61N 5/1065 250/492.1 |
| 9,155,910 B1 | 10/2015 | Sahadevan | |
| 9,470,801 B2 * | 10/2016 | Ziv | A61B 5/055 |
| 9,804,104 B2 * | 10/2017 | Libman | H05B 6/686 |
| 2002/0191746 A1 | 12/2002 | Dinsmore | |
| 2004/0044265 A1 | 3/2004 | Muller et al. | |
| 2004/0079899 A1 | 4/2004 | Ma | |
| 2004/0082855 A1 | 4/2004 | Robar et al. | |
| 2004/0140432 A1 | 7/2004 | Maldonado et al. | |
| 2006/0001855 A1 * | 1/2006 | Lof | G03F 7/70275 355/69 |
| 2006/0106301 A1 | 5/2006 | Kats et al. | |
| 2007/0152610 A1 | 7/2007 | Yakovlev et al. | |
| 2007/0265230 A1 * | 11/2007 | Rousso | A61K 31/66 514/137 |
| 2008/0001090 A1 * | 1/2008 | Ben-Haim | G01T 1/1648 250/363.08 |
| 2008/0002811 A1 | 1/2008 | Allison et al. | |
| 2008/0049897 A1 * | 2/2008 | Molloy | A61N 5/1042 378/65 |
| 2008/0298401 A1 | 12/2008 | Faure et al. | |
| 2009/0185656 A1 | 7/2009 | Heuscher | |
| 2009/0212231 A1 | 8/2009 | Hill et al. | |
| 2009/0225932 A1 | 9/2009 | Zhu et al. | |
| 2009/0252291 A1 | 10/2009 | Lu et al. | |
| 2010/0001200 A1 * | 1/2010 | Ben-Haim | G01T 1/1648 250/394 |
| 2010/0174180 A1 * | 7/2010 | Rousso | A61B 5/417 600/431 |
| 2010/0207042 A1 * | 8/2010 | Harada | A61N 5/1049 250/492.3 |
| 2010/0228116 A1 | 9/2010 | Lu et al. | |
| 2010/0246767 A1 | 9/2010 | Tanabe | |
| 2010/0260317 A1 * | 10/2010 | Chang | A61N 5/103 378/62 |
| 2011/0073778 A1 | 3/2011 | Natori et al. | |
| 2011/0093243 A1 | 4/2011 | Tawhai et al. | |
| 2011/0206187 A1 | 8/2011 | Lee et al. | |
| 2011/0254443 A1 * | 10/2011 | Neubauer | H01J 25/50 315/39.53 |
| 2011/0266464 A1 * | 11/2011 | Takai | G06Q 50/22 250/492.1 |
| 2012/0022363 A1 | 1/2012 | Dempsey | |
| 2012/0085916 A1 | 4/2012 | Clayton et al. | |

(56) References Cited

U.S. PATENT DOCUMENTS

| | | | |
|---|---|---|---|
| 2012/0262333 | A1 | 10/2012 | Trummer |
| 2012/0326636 | A1 | 12/2012 | Eaton et al. |
| 2013/0016814 | A1 | 1/2013 | Treas et al. |
| 2013/0172657 | A1 | 7/2013 | Meier et al. |
| 2013/0231516 | A1* | 9/2013 | Loo .................. A61N 5/1065 600/1 |
| 2013/0287167 | A1 | 10/2013 | Gum et al. |
| 2014/0010351 | A1* | 1/2014 | Rommel ............... G21K 1/02 378/64 |
| 2014/0037541 | A1* | 2/2014 | Rousso ............. A61K 51/0478 424/1.65 |
| 2014/0135563 | A1* | 5/2014 | Loo .................. A61N 5/1065 600/1 |
| 2014/0371581 | A1 | 12/2014 | Mostafavi et al. |
| 2015/0070029 | A1* | 3/2015 | Libman ............... H05B 6/686 324/637 |
| 2015/0087881 | A1 | 3/2015 | Takao et al. |
| 2016/0014876 | A1* | 1/2016 | Tantawi .............. H01P 1/207 315/39 |
| 2016/0193482 | A1 | 7/2016 | Fahrig et al. |
| 2016/0310764 | A1* | 10/2016 | Bharadwaj .......... A61N 5/1078 |

FOREIGN PATENT DOCUMENTS

| | | | |
|---|---|---|---|
| EP | 1358908 | | 11/2003 |
| EP | 3043863 | | 7/2016 |
| EP | 3043864 | | 7/2016 |
| WO | 2005115544 | | 12/2005 |
| WO | 2007140090 | | 12/2007 |
| WO | 2011127946 | | 10/2011 |
| WO | 2012025261 | | 3/2012 |
| WO | 2013133936 | | 9/2013 |
| WO | 2015038832 | | 3/2015 |
| WO | 2015102680 | | 7/2015 |
| WO | WO 2015102681 | A2 * | 7/2015 ............. G05B 15/02 |

OTHER PUBLICATIONS

Papaconstadopoulos et al., "WE-C-BRB-04: Fast and Accurate Hybrid Source Model for Modulated Electron Radiotherap", Medical Physics, vol. 39, No. 6, Jun. 2012, p. 3944.

International Search Report and Written Opinion dated Apr. 19, 2013 in International Patent Application No. PCT/US2013/025765; 20 pages.

International Search Report and Written Opinion dated Jul. 2, 2015 in International Patent Application No. PCT/US2014/055260; 7 pages.

International Search Report and Written Opinion dated Jul. 9, 2015 in International Patent Application No. PCT/US2014/055252; 8 pages.

International Search Report and Written Opinion dated Jan. 27, 2015 in International Patent Application No. PCT/US2014/055270; 16 pages.

Bazalova, M., et al., "WE-C-BRB-05: Monte Carlo Simulations and Experimental Validation of Rapid Dose Delivery with Very High-Energy Electron Beams"; and Papaconstadopoulos, P., et al., "WE-C-BRB-04: Fast and Accurate Hybrid Source Model for Modulated Electron Radiotherapy"; Medical Physics, vol. 39, No. 6, Jun. 2012, p. 3944.

DesRosiers, C., et al., "150-250 MeV electron beams in radiation therapy", Physics in Medicine and Biology, vol. 45, No. 7, 2000, pp. 1781-1805.

DesRosiers, Colleen M., "An evaluation of very high energy electron beams (up to 250 MeV) in radiation therapy", Dec. 2004, 163 pages.

Fuchs, Thomas, "Laser-accelerated particles: Investigations towards applications in radiotherapy", 2007, 152 pages.

Fuchs, T., et al., "Treatment planning for laser-accelerated very-high energy electrons." Physics in Medicine and Biology vol. 54, No. 11, 2009, pp. 3315-3328.

Glinec, Yannick, et al., "Radiotherapy with laser-plasma accelerators: Monte Carlo simulation of dose deposited by an experimental quasimonoenergetic electron beam", Medical Physics, vol. 33, No. 1, Jan. 2006, pp. 155-162.

Yeboah, C., et al., "Optimization of intensity-modulated very high energy (50-250 MeV) electron therapy", Physics in Medicine and Biology, vol. 47, No. 8, 2002, pp. 1285-1301.

Yeboah, C., et al., "Optimized treatment planning for prostate cancer comparing IMPT, VHEET and 15 MV IMXT", Physics in Medicine and Biology, vol. 47, No. 13, 2002, pp. 2247-2261.

Walters, B. et al., "DOSXYZnrc Users Manual," Ionizing Radiation Standards National Research Council of Canada, 2011, pp. 1-109, http://irs.inms.nrc.ca/software/beamnrc/documentation/pirs794.

Howell, Rebecca M. et al., "Measurements of secondary neutron dose from 15 MV and 18 MV IMRT," Radiation Protection Dosimetry, 2005; vol. 115, issues 1-4, pp. 508-512, abstract only.

Neilson, Jeffrey et al., "Design of RF feed system and cavities for standing-wave accelerator structure," Nuclear Instruments and Methods in Physics Research A: Accelerators, Spectrometers, Detectors and Associated Equipment, Nov. 2011, vol. 657, issue 1, pp. 52-54, abstract only.

Palowitz, Denise B. et al., "MCNPX 2.7.E Extension," Los Alamos National Laboratory report LA-UR-11-01502, Mar. 2011, draft of later publication Palowitz, Denise B. et al., "MCNPX User's Manual, Version 2.7.0," Los Alamos National Laboratory report LA-CP-11-00438, Apr. 2011, (http://mcnpx.lanl.gov/documents.html).

Schneider, Uwe et al., "Secondary neutron dose during proton therapy using spot scanning," International Journal of Radiation Oncology Biology Physics, 2002, vol. 53, issue 1, pp. 244-251, abstract only.

Tantawi, Sami G., "rf distribution system for a set of standing-wave accelerator structures," Physical Review Special Topics—Accelerators and Beams, 2006, vol. 9, No. 11, pp. 112001-1-112001-6 (http://prst-ab.aps.org/abstract/PRSTAB/v9/i11/e112001).

Dolgashev Valery et al., "Geometric dependence of radio-frequency breakdown in normal conducting accelerating structures," Applied Physics Letters, 2010, vol. 97, No. 17, (http://apl.aip.org/resource/1/applab/v97/i17/p171501_s1).

Caryotakis, George, "Development of X-band Klystron Technology at SLAC," Proceedings of the 1997 Particle Accelerator Conference, May 1997, Vancouver, B.C., CA, vol. 3, pp. 2894-2898 (http://www.slac.stanford.edu/cgi-wrap/getdoc/slac-pub-7548.pdf).

Furukawa et al., "Design study of a raster scanning system for moving target irradiation in heavy-ion radiotherapy", Medical Physics vol. 34, No. 3, Mar. 2007, pp. 1085-1097.

Ulmer, "On the Creation of High Energy Bremsstrahlung and Intensity by a Multitarget and Repeated Focusing of the Scattered Electrons by a Small-Angle Backscatter at the Wall of a Cone and Magnetic Fields—A Possible Way to Improve Linear Accelerators in Radiotherapy and to verify Heisenberg-Euler scatter", Radiation Physics and Chemistry 81 (2012), pp. 387-402.

\* cited by examiner

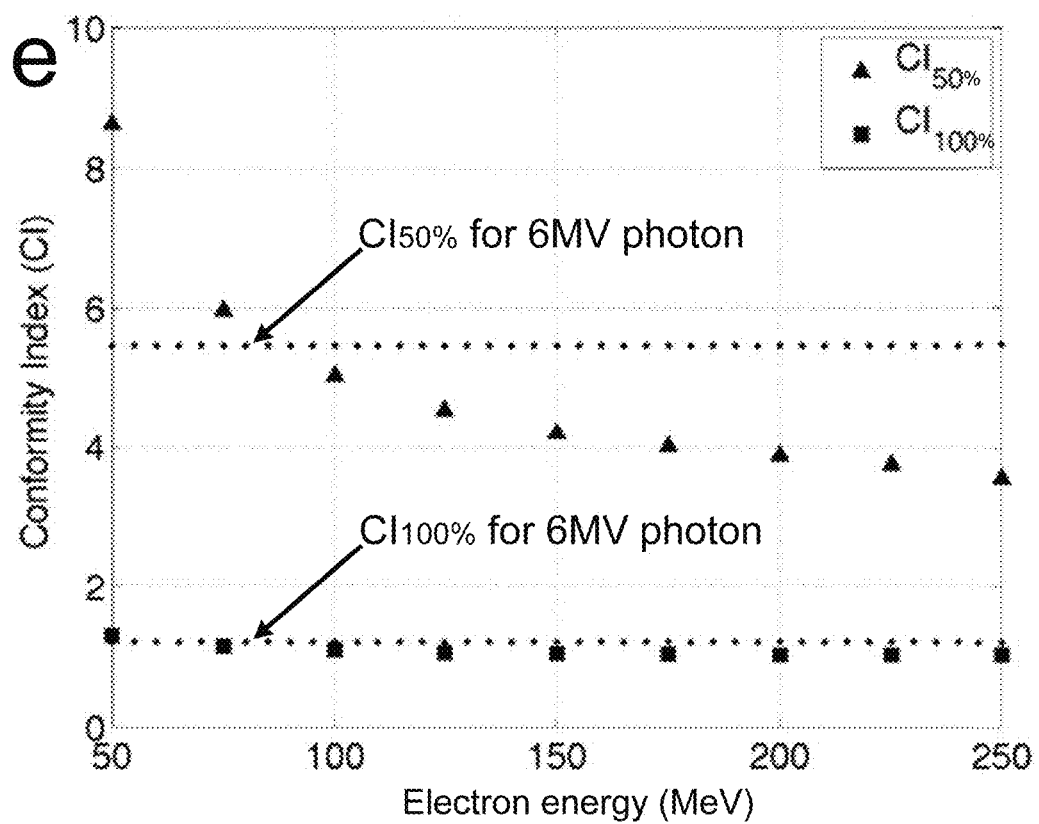
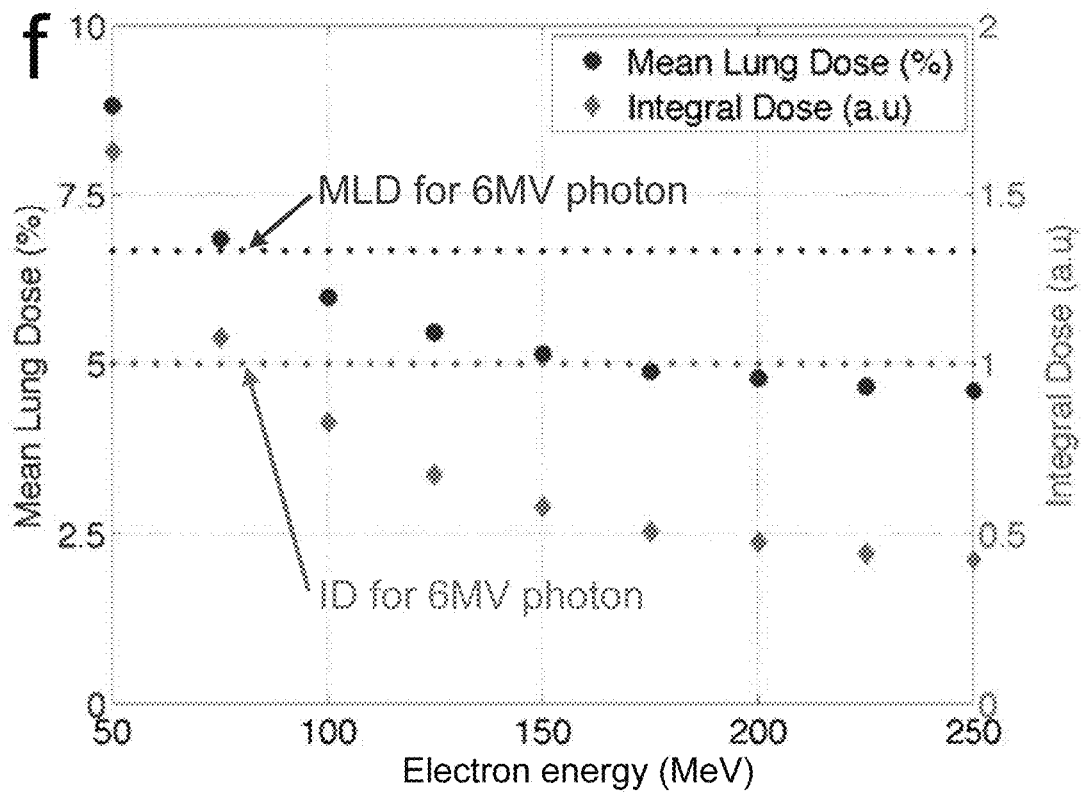
FIG. 2

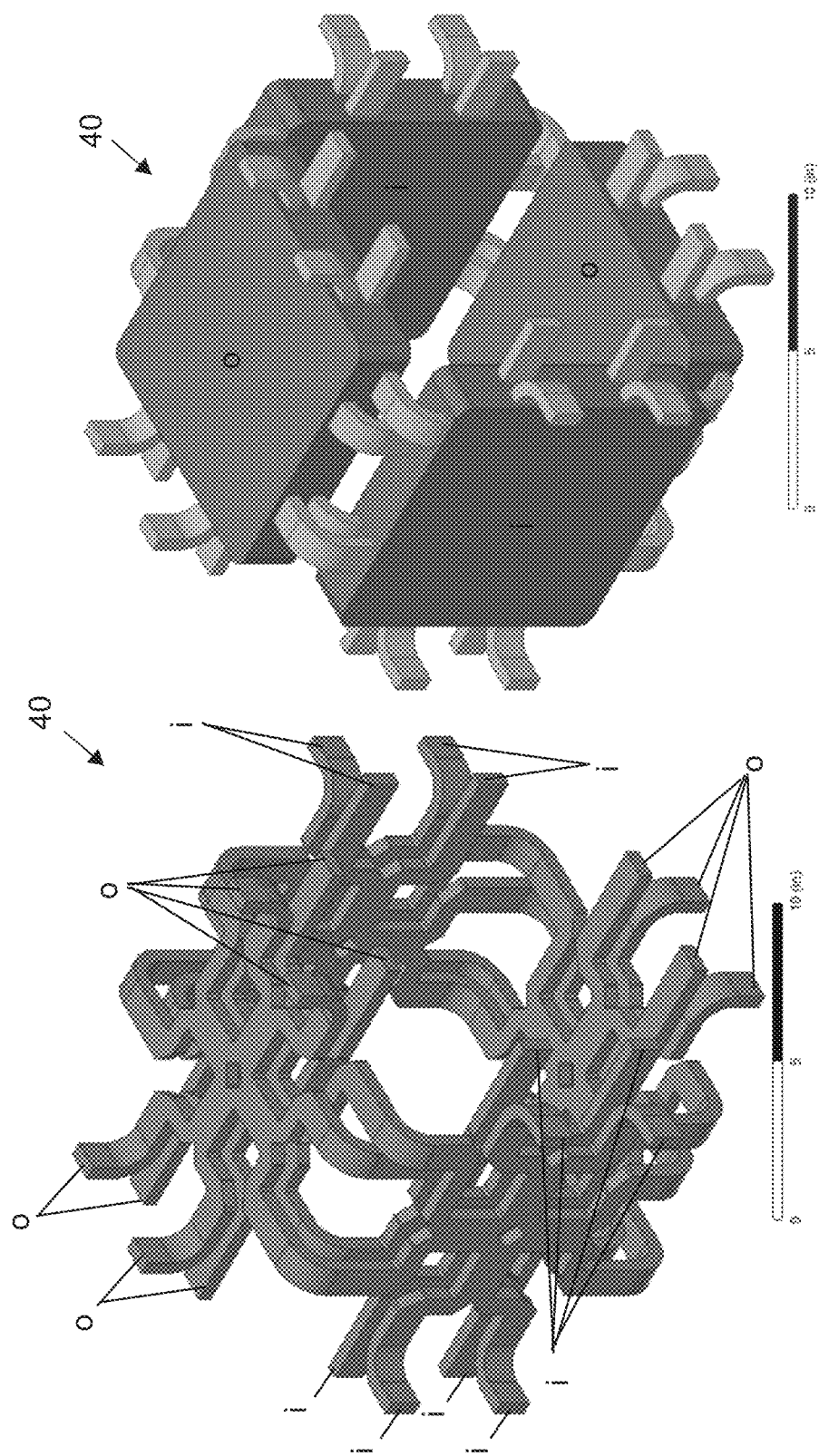

METHODS AND SYSTEMS FOR RF POWER GENERATION AND DISTRIBUTION TO FACILITATE RAPID RADIATION THERAPIES

CROSS-REFERENCES TO RELATED APPLICATIONS

This application is a continuation of PCT/US2014/055260, filed Sep. 11, 2014, which application claims priority to U.S. Provisional Application No. 61/876,679 filed Sep. 11, 2013; U.S. Provisional Application No. 62/003,002 filed May 26, 2014; and U.S. Provisional Application No. 62/022,469 filed Jul. 9, 2014, each of which is incorporated herein by reference in its entirety.

This application is generally related to U.S. application Ser. No. 13/765,017, entitled "Pluridirectional Very High Electron Energy Radiation Therapy Systems and Processes," filed Feb. 12, 2013 and PCT Application No. PCT/US2014/055252, filed Sep. 11, 2014, and PCT/US2014/055270, filed Sep. 11, 2014; the full disclosures of which are incorporated herein by reference in their entirety.

FIELD OF THE INVENTION

The invention generally relates to radiation therapies and more particularly to systems and methods for facilitating rapid radiation therapies.

BACKGROUND OF THE INVENTION

Major technical advances in radiation therapy in the past two decades have provided effective sculpting of 3-D dose distributions and spatially accurate dose delivery by imaging verification. These technologies, including intensity modulated radiation therapy (IMRT), hadron therapy, and image guided radiation therapy (IGRT) have translated clinically to decreased normal tissue toxicity for the same tumor control, and more recently, focused dose intensification to achieve high local control without increased toxicity, as in stereotactic ablative radiotherapy (SABR) and stereotactic body radiotherapy (SBRT).

One key remaining barrier to precise, accurate, highly conformal radiation therapy is patient, target and organ motion from many sources including musculoskeletal, breathing, cardiac, organ filling, peristalsis, etc. that occurs during treatment delivery, currently 15-90 minutes per fraction for state-of-the-art high-dose radiotherapy. As such, significant effort has been devoted to developing "motion management" strategies, e.g., complex immobilization, marker implantation, respiratory gating, and dynamic tumor tracking.

BRIEF SUMMARY OF THE INVENTION

The present invention relates to methods and systems for facilitating radiation therapies, particularly extremely rapid radiation therapies that rapidly deliver a radiation treatment sufficiently fast enough to freeze physiologic motion.

In one aspect, the invention relates to a power distribution system for powering multiple accelerators that includes: multiple RF power sources; multiple accelerating structures; an RF phase array coupling the RF power sources with the accelerating structures; and a programmable controller operatively coupled with the RF phase array to control a phase and an amplitude of the RF phase array such that a total RF energy from the RF power sources is directed to a select accelerating structure of the array through source phasing. In some embodiments, the controller is configured to rapidly adjust the source phasing of the RF array so as to direct the total RF power from the RF power sources between multiple accelerating structures in rapid succession. The controller may be configured to adjust the source phasing of the RF array sufficiently rapid so as to direct an entire treatment dosage to a targeted tissue of a patient from multiple accelerating structures of the array in less than 10 seconds. In some embodiments, each of the RF power sources provides less power than that required to operate any single accelerating structure of the array. In one aspect, each of the power sources operates at 100 kV or less. The total peak RF power provided by the multiple sources through the phase array may be 50 MW or greater. Each of the power sources may include a pulse compressor to boost a peak power output.

The RF power sources may be an amplifier type source, phase locked oscillator, externally phase locked magnetron, linear devices and/or cross field devices or a multi-klystron device, particularly multi-klystron devices that are overmolded.

In some embodiments, a power distribution in accordance with the invention include multiple inputs that that the multiple power sources are fed into a passive microwave network, each input corresponding to one of the power sources. The network may comprise a scattering matrix representation that isolates inputs from each other. In one aspect, the network may be of a symmetrical design so that the outputs of the multiple power sources are isolated from each other.

In another aspect, the invention relates to methods of powering a first single accelerator of an array of accelerators with multiple power source/amplifiers through an RF phase array coupling multiple RF power sources to the array of accelerators, when substantially a total energy output from the multiple power source/amplifiers are directed to the single accelerator based on a source phasing of the RF phase array, each power source/amplifier providing less power than that required to operate the single accelerator; and varying the source phasing of the RF phase array so as to direct substantially the total energy output from the multiple power sources to a second single accelerator of the plurality. Varying the source phasing of the RF phase array may be performed with a controller rapidly enough so as to allow an entire treatment dosage to be directed to a targeted tissue of a patient from multiple accelerating structures in less than 10 seconds.

In yet another aspect, the invention relates to a multi-beam system for producing high energy treatment beams using a low voltage power source that include multiple klystrons sealed within a common vacuum envelope, an input combiner extending between each of multiple klystrons that defines a buncher cavity for each of the klystrons; and an output combiner extending between each of the multiple klystrons that defines a catcher cavity for each of the klystrons. In one advantageous aspect, the device is overmolded. The input combiner has a common cavity such that the buncher cavity of each klystron is in communication with each other thereby allowing input into each klystron through a single input. The output combiner has a common cavity such that the catcher cavity of each klystron is in communication with each other, thereby allowing combining of the beams of each klystron and output of the combined beam though a single output. In one aspect, the klystrons of the device are arranged in a linear array or a rectangular array. Each of the klystrons may include focusing device, such as permanent magnets, generally without requiring use of a focusing solenoid. In some embodiments, the multi-beam device uses gridded cathodes.

In another aspect, the invention relates to a multi-beam system comprising a power distribution system for powering the plurality of klystrons that includes multiple RF power sources; an RF phase array coupling the multiple RF power sources with the klystrons; and a programmable controller operatively coupled with the RF phase array so as to automatically control a phase of the RF phase array such that a total RF energy from the multiple RF power sources is directed to select klystrons of the plurality through source phasing. Automatic control allows the power to be rapidly switched between select accelerators so as to allow deliver of an entire treatment dose from multiple differing angles in less than 10 seconds, preferably within one second or less.

Delivery of radiation therapies in significantly reduced time-scale as compared to convention methods poses a number of difficulties, many of which are addressed by the methods and systems described herein. For example, aspects relating to targeted tissue motion, radiation beam generation and steering, power production and distribution, radiation source design, radiation beam control and shaping/intensity-modulation, treatment planning, imaging and dose verification present various challenges and, as used in conventional therapies, barriers to delivering radiation therapies to targeted tissues on a significantly reduced time scale. While the methods and systems described herein may be used to facilitate very rapid radiation therapies, particularly by addressing the above noted aspects of radiation delivery therapies, it is understood that these methods and systems are not limited to any particular radiation therapy delivery system or application described herein, and may be advantageous when used in various other radiation therapies and delivery systems, including conventional radiation therapies as well as non-medical applications.

A fundamentally different approach to managing motion is to deliver the treatment so rapidly that no significant physiologic motion occurs between verification imaging and completion of treatment. According to certain embodiments of the invention, an accelerator, more preferably a compact high-gradient, very high energy electron (VHEE) linear accelerator, which may be a standing wave linear accelerator, together with a delivery system capable of treating patients from multiple beam directions, potentially using all electromagnetic or radiofrequency deflection steering is provided, that can deliver an entire dose or fraction of high-dose (e.g., 20-30 Gy) radiation therapy sufficiently fast to freeze physiologic motion, yet with a better degree of dose conformity or sculpting than conventional photon therapy. The term "sufficiently fast to freeze physiologic motion" in this document means preferably faster than one human breath hold, more preferably less than 10 seconds, even more preferably less than 5 seconds, even more preferably less than one heartbeat and most preferably less than a second. In addition to the unique physical advantages of extremely rapid radiation delivery, there may also be radiobiological advantages in terms of greater tumor control efficacy for the same physical radiation dose. Certain embodiments of the invention can also treat non-tumor targets, such as, by way of nonlimiting example, ablation or other treatment of: (1) nerves or facet joints for pain control; (2) foci in the brain for neuromodulation of neurologic conditions including pain, severe depression, and seizures; (3) portions of the lung with severe emphysema; and/or (4) abnormal conductive pathways in the heart to control refractory arrhythmias.

In certain embodiments, the controller is configured to receive information from an imaging device and use the information from the imaging device to control the directions in which the beam steering device steers the beam to the target. In some embodiments, the accelerator is a linear electron accelerator capable of generating a beam having energy of between 1 and 250 MeV, more preferably 50 and 250 MeV and most preferably between 75 and 100 MeV. In a rapid radiation treatment embodiment, the time period is preferably faster than one human breath hold, more preferably less than 10 seconds, even more preferably less than 5 seconds, even more preferably less than one heartbeat and most preferably less than a second.

BRIEF DESCRIPTION OF THE DRAWINGS

FIGS. 13A-13B illustrate an example phase array device for use in an RF power distribution system in accordance with aspects of the invention.

DETAILED DESCRIPTION OF THE INVENTION

I. Rapid Radiation Treatment

A. Significance

Figure 1:
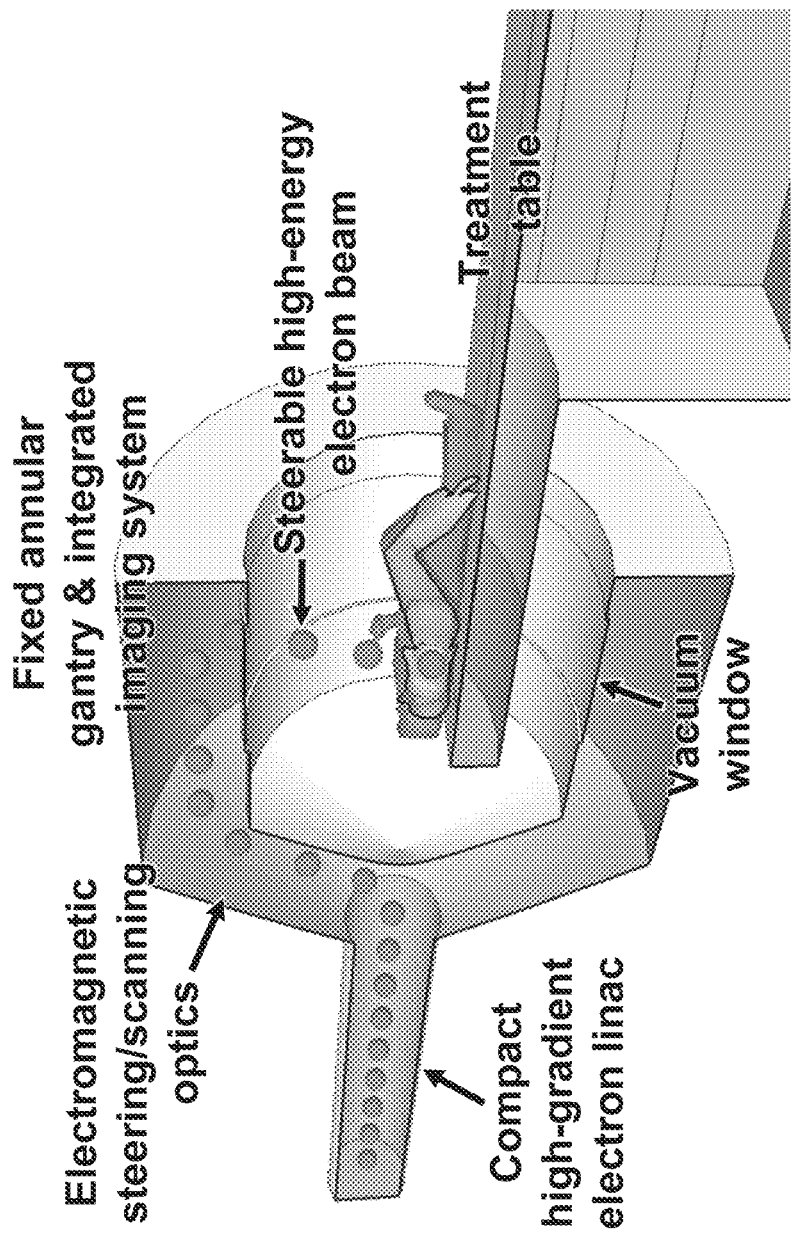
FIG. 1 is a schematic representation of a system in accordance with certain embodiments of the invention, showing beam access from a large number of axial directions by electromagnetic- or radiofrequency deflection steering.

In the U.S., cancer has surpassed heart disease as the leading cause of death in adults under age 85, and of the 1.5 million patients diagnosed with cancer each year, about two thirds will benefit from radiation therapy (RT) at some point in their treatment, with nearly three quarters of those receiving RT with curative intent. Worldwide, the global burden of cancer is increasing dramatically owing to the aging demographic, with an incidence of nearly 13 million per year and a projected 60% increase over the next 20 years, and the number of patients who could benefit from RT far exceeds its availability. Moreover, even when RT is administered with curative intent, tumor recurrence within the local radiation field is a major component of treatment failure for many common cancers. Thus, improvements in the efficacy of and access to RT have tremendous potential to save innumerable lives.

Although there have been major technological advances in radiation therapy in recent years, a fundamental remaining barrier to precise, accurate, highly conformal radiation therapy is patient, target, and organ motion from many sources including musculoskeletal, breathing, cardiac, organ filling, peristalsis, etc. that occurs during treatment delivery. Conventional radiation delivery times are long relative to the time scale for physiologic motion, and in fact, more sophisticated techniques tend to prolong the delivery time, currently 15-90 minutes per fraction for state-of-the-art high-dose radiotherapy. The very fastest available photon technique (arc delivery with flattening filter free mode) requires a minimum of 2-5 min to deliver 25 Gy. Significant motion can occur during these times.

Even for organs unaffected by respiratory motion, e.g., the prostate, the magnitude of intrafraction motion increases significantly with treatment duration, with 10% and 30% of treatments having prostate displacements of >5 mm and >3 mm, respectively, by only 10 minutes elapsed time. As such, considerable effort has been devoted to developing "motion management" strategies in order to suppress, control, or compensate for motion. These include complex immobilization, fiducial marker implantation, respiratory gating, and dynamic tumor tracking, and in all cases still require expansion of the target volume to avoid missing or undertreating the tumor owing to residual motion, at the cost of increased normal tissue irradiation.

Several factors contribute to long delivery times in existing photon therapy systems. First, production of x-rays by Bremsstrahlung is inefficient, with less than 1% of the energy of the original electron beam being converted to useful radiation. Second, collimation, and particularly intensity modulation by collimation, is similarly inefficient as the large majority of the beam energy is blocked by collimation. Third, using multiple beam angles or arcs to achieve conformal dose distributions requires mechanical gantry motion, which is slow. Treatment using protons or other heavier ions has dosimetric advantages over photon therapy, and these particles can be electromagnetically scanned very rapidly across a given treatment field. However changing beam directions still requires mechanical rotation of the massive gantry, which is much larger and slower than for photon systems. The cost and size of these systems also greatly limits their accessibility.

Very high-energy electrons (VHEE) in the energy range of 50-250 MeV have shown favorable dose deposition properties intermediate between megavoltage (MV) photons and high-energy protons. Without the need for inefficient Bremsstrahlung conversion or physical collimation, and with a smaller steering radius than heavier charged particles, treatment can be multiple orders of magnitude faster than any existing technology in a form factor comparable to conventional medical linacs. According to certain embodiments of the invention, a compact high-gradient VHEE accelerator and delivery system is provided that is capable of treating patients from multiple beam directions with great speed, using electro-magnetic, radiofrequency deflection or other beam steering devices. Such embodiments may deliver an entire dose or fraction of high-dose radiation therapy sufficiently fast to freeze physiologic motion, yet with a better degree of dose conformity or sculpting, and decreased integral dose and consequently decreased risk of late toxicities and secondary malignancies, than the best MV photon therapy. Suitable energy ranges in accordance with certain embodiments of the invention are 1-250 MeV, more preferably 50-250 MeV, and most preferably 75-100 MeV. Again, as described in the Summary section above, the term "sufficiently fast to freeze physiologic motion" in this document means preferably faster than one human breath hold, more preferably less than 10 seconds, even more preferably less than 5 seconds, even more preferably less than one heartbeat and most preferably less than a second.

According to some embodiments, a major technological advance is extremely rapid or near instantaneous delivery of high dose radiotherapy that can eliminate the impact of target motion during RT, affording improved accuracy and dose conformity and potentially radiobiological effectiveness that will lead to improved clinical outcomes. Rapid imaging and treatment can also lead to greater clinical efficiency and patient throughput. For standard treatments, the room occupancy time can be reduced to less than 5 minutes. There can also be a great practical advantage for special populations like pediatric patients who normally require general anesthesia for adequate immobilization during long treatments, and who can instead be treated with only moderate sedation for such rapid treatments. Such advantages can be achieved, according to some embodiments, in a compact physical form factor and low cost comparable to conventional photon therapy systems, and much lower than hadron therapy systems. One embodiment is shown in FIG. 1, which shows a system wherein beam access from a large number of axial directions is achieved by electromagnetic steering without moving parts or with a minimum of moving parts, for extremely fast highly conformal radiotherapy. The system shown in FIG. 1 includes a compact linear accelerator, a beam steering device, and a controller for controlling the very high electron energy beam that is delivered to the patient. The embodiment can also include an integrated imaging device that obtains images of portions of the patient including the tumor or other site to be treated. The imaging device can also provide information to allow for control of the beam steering device in order to control directions from which the beam is delivered, and timing of the beam, among other variables.

Furthermore, the prolonged treatment times of conventional highly conformal RT are sufficiently long for repair of sublethal chromosomal damage to occur during treatment, potentially reducing the tumoricidal effect of the radiation dose. Thus in addition to the unique physical advantages of extremely rapid radiation delivery, there may also be dose advantages. It is hypothesized that the treatment times sufficiently fast to freeze physiologic motion that are made possible by certain embodiments of the invention may be more biologically effective, producing enhanced tumor cell killing for the same physical dose. Differences between certain embodiments of the invention and conventional photon therapy that impact biological effectiveness include a much faster delivery time and differences in the radiation quality.

Dose rate effects are well described in the radiobiology literature, in which prolongation of delivery times results in decreased cell killing. The main mechanism known to be responsible for this effect is repair of potentially lethal DNA double strand breaks (DSB) during the interval over which a given dose of radiation is delivered. Several in vitro studies have demonstrated significantly decreased cell killing when delivery is protracted from a few minutes to tens of minutes. However, there is a lack of consensus in the literature regarding the kinetics of sublethal damage (SLD) repair, with some studies suggesting that components of SLD repair may have repair half-times of as little as a few minutes. If so, shortening the delivery times even from a few minutes to a time period sufficiently fast to freeze physiologic motion has the potential to increase tumor cell killing.

B. Beam Steering

Some embodiments of the invention take advantage of the fact that electrons are relatively easier to manipulate using electric and magnetic fields. Charged particles such as electrons and protons can be produced as spatially coherent beams that can be steered electromagnetically or with radiofrequency deflection with high rapidity. Thus, direct treatment with scanned charged particle beams can eliminate the inefficiencies of Bremsstrahlung photon multiple beams from different directions toward the target in the patient. All conventional radiation therapy systems accomplish multidirectional treatment by mechanically rotating a gantry, or an entire compact linac, or even cyclotron, directing radiation to the target from one direction at a time.

As a preliminary matter, at the end of the accelerator structure the beam must be deflected and then transported to the exit port and toward a target in or on the patient, such as a tumor in the patient. At the exit port the beam must be steered again to change the exit angle and/or beam size to adapt to the treatment plan. Electro-magnetic and/or RF deflector steering systems will manipulate the electron beam.

A variety of gantry designs are potentially available, from simple to complex, ranging from multiple discrete beam ports arranged around the patient to a continuous annular gantry to allow arbitrary incident axial beam angles. The design depends on a number of factors, including scanning strategies such as thin pencil beam raster scanning vs. volume filling with non-isocentric variable-size shots, or use of transverse modulation of the electron beam profile.

According to one embodiment, the steering system of the electron beam starts at the end of the accelerator structure with a two-dimensional deflector, which guides the beam into one of multiple channels. Once the beam enters a specific channel it is guided all the way to the exit of the channel, which is perpendicular to the axis of the patient. The guidance through the channels is achieved using low aberration electron optics. At the exit of each channel another small 2-D deflector can be added to scan the beam over a target. The number of channels can then be about 10-50. For a given channel width, a larger initial deflection would increase the number of channel entry ports that fit into the circumference swept by the beam. Thus if the field strength were increased, the number of channels could be increased to 100 or more.

Because a linear accelerator will typically consume 50 to 100 MW of peak power to achieve 100 MeV of acceleration, over a length of 2 to 1 m respectively, potential megawatt-powered RF deflectors can be considered. These have the advantage of being ultra-fast and permit capitalization on the RF infrastructure that is used for the main accelerator structure. In any event, the delivery system is preferably optimized to achieve high-dose treatment times sufficiently fast to freeze physiologic motion.

Beam steering systems according to certain embodiments of the invention adopt a design that uses a smaller number of discrete beam channels, for example 3-10, that are mechanically rotated with the gantry around the patient. The initial deflector at the exit of the accelerator rapidly steers beams into the channels as they rotate. Although the ideal is to eliminate the need for any mechanical moving parts, some advantages of this design include: arbitrary rotational angular resolution despite a fixed number of beam channels; reduced complexity and possibly cost given the smaller number of beam channels needed to achieve equivalent angular coverage; and the larger space between beam channels which makes it more straightforward to incorporate an x-ray source and detecting array for imaging, which when rotated provides integrated computed tomography imaging. The rate of mechanical rotation preferably provides full angular coverage sufficiently fast to freeze physiologic motion. The greater the number of beam channels, the less rotational speed required to meet this condition as a general matter.

One innovation of certain embodiments of the invention is to eliminate mechanical gantry rotation, thus a beam steering system with no mechanical moving parts. One such embodiment is illustrated in FIG. 1, in which there is a gantry through which a charged particle beam is electro-magnetically steered or steered using radiofrequency deflection to the target from any axial direction and a limited range of non-coplanar directions in addition. An alternative implementation is to use multiple discrete beam ports arranged radially around the patient, with the beam being steered through each of the ports to the target for multidirectional beam arrangements. Another alternative implementation is to have multiple accelerating structures, one for each of a set of beam ports arranged radially around the patient.

Such novel treatment system geometries and steering systems can greatly enhance the treatment delivery speed of radiation therapy using any type of charged particle. Combining it with high-energy electrons in the 1-250 MeV range, more preferably the 50-250 MeV range, most preferably the 75-100 MeV range, has the following additional advantages: (1) Conformal dose distributions to both superficial and deep targets in patients superior to what can be achieved with conventional high-energy photon therapy; (2) Compactness of the source and power supply, which by using high-gradient accelerator designs such as those based wholly or partially on accelerators developed or in development at the SLAC National Accelerator Laboratory (SLAC) as further below can accelerate electrons up to these energies in less than 2 meters; (3) Compactness of the gantry/beam ports compared to protons or ions because of the smaller electromagnetic fields needed for electrons. This results in a system of comparable cost and physical size to existing conventional photon radiotherapy treatment systems, yet with better dose distributions and far faster dose delivery.

If treatment with photon beams is still desired, an alternative embodiment is to incorporate in this geometry an array of high density targets and collimator grid in place of a single target/multi-leaf collimator combination, one per beam port in the case of discrete beam ports, or mounted on a rapidly rotating closed ring and targeted by the scanned electron beam in the case of an annular beam port, in order to produce rapidly scanned, multidirectional photon beams. While this approach may be subject to the inefficiency of Bremsstrahlung conversion, the speed limitations of conventional mechanical gantry and multi-leaf collimator motions may be essentially eliminated. The main potential advantage of this implementation is that existing commercial electron linacs in a lower energy range could be used as the source.

In addition to extremely rapid dose delivery, certain embodiments of the invention naturally facilitate rapid image-guidance to ensure accuracy. By adjusting the energy of the scanned electron beam and directing it to an annular target or a fixed array of targets, with an appropriately arranged detector array, extremely fast x-ray computed tomography (CT) or digital tomosynthesis images can be obtained and compared to pre-treatment planning images immediately before delivery of the dose. Alternative embodiments can include integration of more conventional x-ray imaging or other imaging modalities, positron emission tomography and other options described further below.

C. Monte Carlo Simulation Design Considerations

One approach in designing certain embodiments of the invention is to proceed using some or all of the following: (1) Monte Carlo simulations to determine optimal operating parameters; (2) experimental measurements of VHEE beams to validate and calibrate the Monte Carlo codes; (3) implementation factors for practical, cost-efficient and compact designs for the systems; and (4) experimental characterization of key radiobiological aspects and effects.

1. Monte Carlo (MC) Simulation

MC simulations of VHEE of various energies have been performed on a sample case to estimate the range of electron energies needed to produce a plan comparable to optimized photon therapy. Dose distributions were calculated for a simulated lung tumor calculated on the CT data set of an anthropomorphic phantom.

Specifically, an optimized 6 MV photon beam Volumetric Modulated Arc Therapy Stereotactic Ablative Body Radiotherapy (VMAT SABR) plan calculated in the Eclipse treatment planning system, and simplistic conformal electron arc plans with 360 beams using a commonly available 20 MeV energy and a very high 100 MeV energy calculated with the EGSnrc MC code were compared. (See Walters B, Kawrakow I, and Rogers DWO, DOSXYZnrc, Users Manual, 2011, Ionizing Radiation Standards National Research Council of Canada. p. 1-109, available online at (http://irs.inms.nrc.ca/software/beamnrc/documentation/pirs794/), incorporated herein by this reference).

Figure 2:
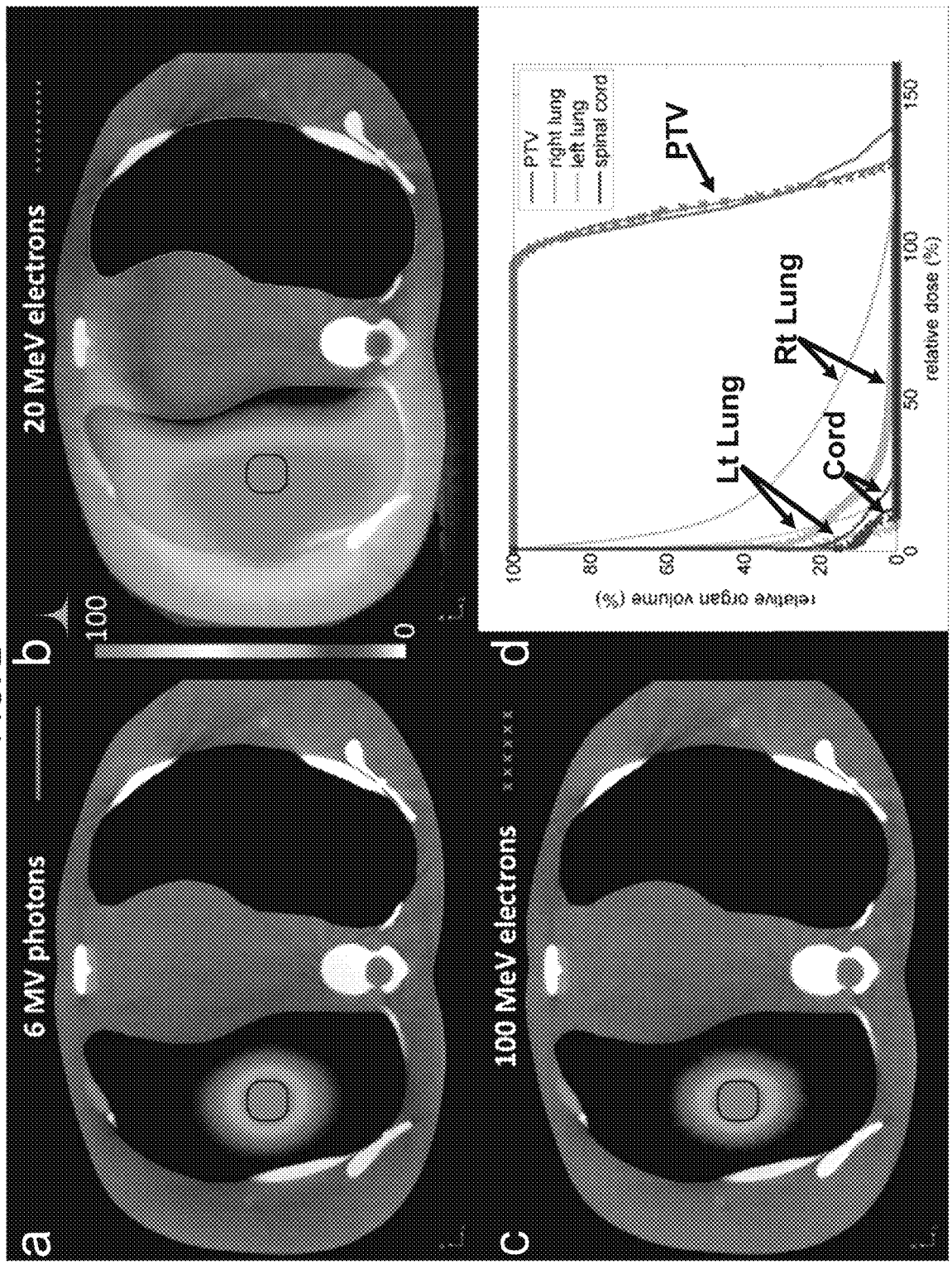
FIG. 2 shows comparative simulation results of SABR for an early stage lung tumor using 6 MV photons, 20 MeV electrons, and 100 MeV electrons.

FIG. 2 shows axial images of simulation of SABR for an early stage lung tumor: dose distribution in an anthropomorphic phantom for a state-of-the-art 6 MV photon VMAT plan (FIG. 2a), a conformal electron arc plan using currently available 20 MeV electron beam (FIG. 2b), and a conformal electron arc plan using a 100 MeV electron beam as might be delivered by an embodiment of the invention (FIG. 2c). A graphical representation shows dose volume histogram ("DVH") of the planning target volume ("PTV") (delineated in black in the axial images) and critical organs: DVHs for 6 MV photons are shown in solid, 20 MeV electrons in dotted, and 100 MeV electrons in crossed lines (FIG. 2d). The plans were normalized to produce the same volumetric coverage of the PTV by the prescription dose. While conventional 20 MeV electrons results in poor conformity, the 100 MeV electron plan, even without optimization, is slightly more conformal than the 6 MV photon VMAT plan. Simulating conformal electron arcs across an energy range of 50-250 MeV (FIGS. 2e, 2f) demonstrates that both the high (100%) and intermediate (50%) dose conformity indices (CI100% and CI50%) as well as the mean lung dose and total body integral dose are superior for electron energies of ~80 MeV and higher for this selected clinical scenario. With inverse optimization, superior plans with even lower electron energies should be possible.

As shown in FIG. 2, the axial views of the dose distributions demonstrate that when all the plans are normalized to produce the same volumetric coverage of the target, the dose conformity of the 20 MeV beam is poor whereas the 100 MeV electron beam, even without inverse optimization, generates a dose distribution equivalent to the state-of-the-art 6 MV photon beam VMAT plan. In fact, the DVH's of the target and critical structures for the three beams demonstrate slightly better sparing of critical structures with the 100 MeV electron plan compared to the 6 MV photon plan. As shown in FIGS. 2e and 2f, at electron energies above ~80 MeV, simple conformal electron arc plans (normalized to produce the same volumetric coverage of the target) are superior to the optimized 6 MV photon VMAT plan in terms of conformity, with conformity index defined as the ratio of the given percent isodose volume to the PTV, and the normal organ doses (mean lung dose) and total body integral dose (expressed in arbitrary units normalized to the photon plan). In preliminary simulations of this selected clinical scenario, the inventors have found electron energies of 75-100 MeV to produce plans of comparably high to superior quality compared to the best photon plans, and anticipate that plan optimization will produce superior plans with even lower electron energies. For example, the inventors have used Monte Carlo simulations to demonstrate that an 8 cc lung tumor could be treated with 100 MeV electrons to a dose of 10 Gy in 1.3 seconds.

Further optimization of the electron plan can help to define the minimum electron beam energy with a comparable dose distribution to the best photon VMAT plan. In preliminary simulations of this selected clinical scenario, the inventors have found electron energies of 75-100 MeV to produce plans of comparably high quality to the best photon plans, and anticipate superior plans with plan optimization.

2. Experimental Measurement of VHEE Beams a. Monte Carlo Simulations

Figure 3A:
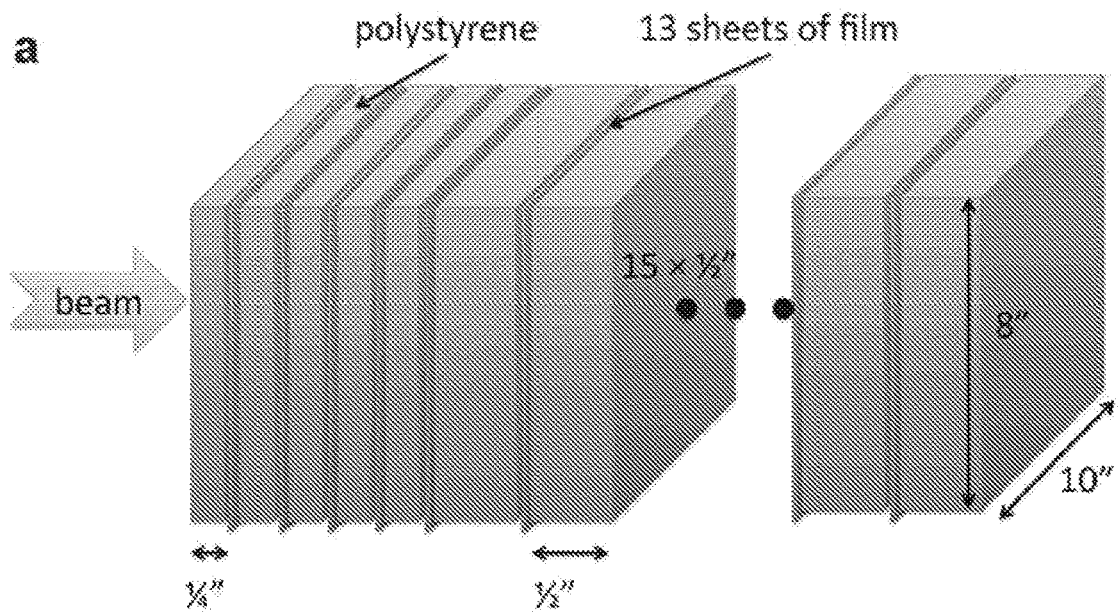
FIG. 3 is a schematic (a) and photograph (b) of the experimental setup for film measurements (c) of very high energy electron beams at the Next Linear Collider Test Accelerator (NLCTA) beam line at the SLAC National Accelerator Laboratory (SLAC), together with Monte Carlo simulations (solid lines) and film measurements (markers) of percentage depth dose curves (d) and beam profiles taken at 6 mm depth (e) for 50 MeV and 70 MeV beams, respectively.
Figure 3B:
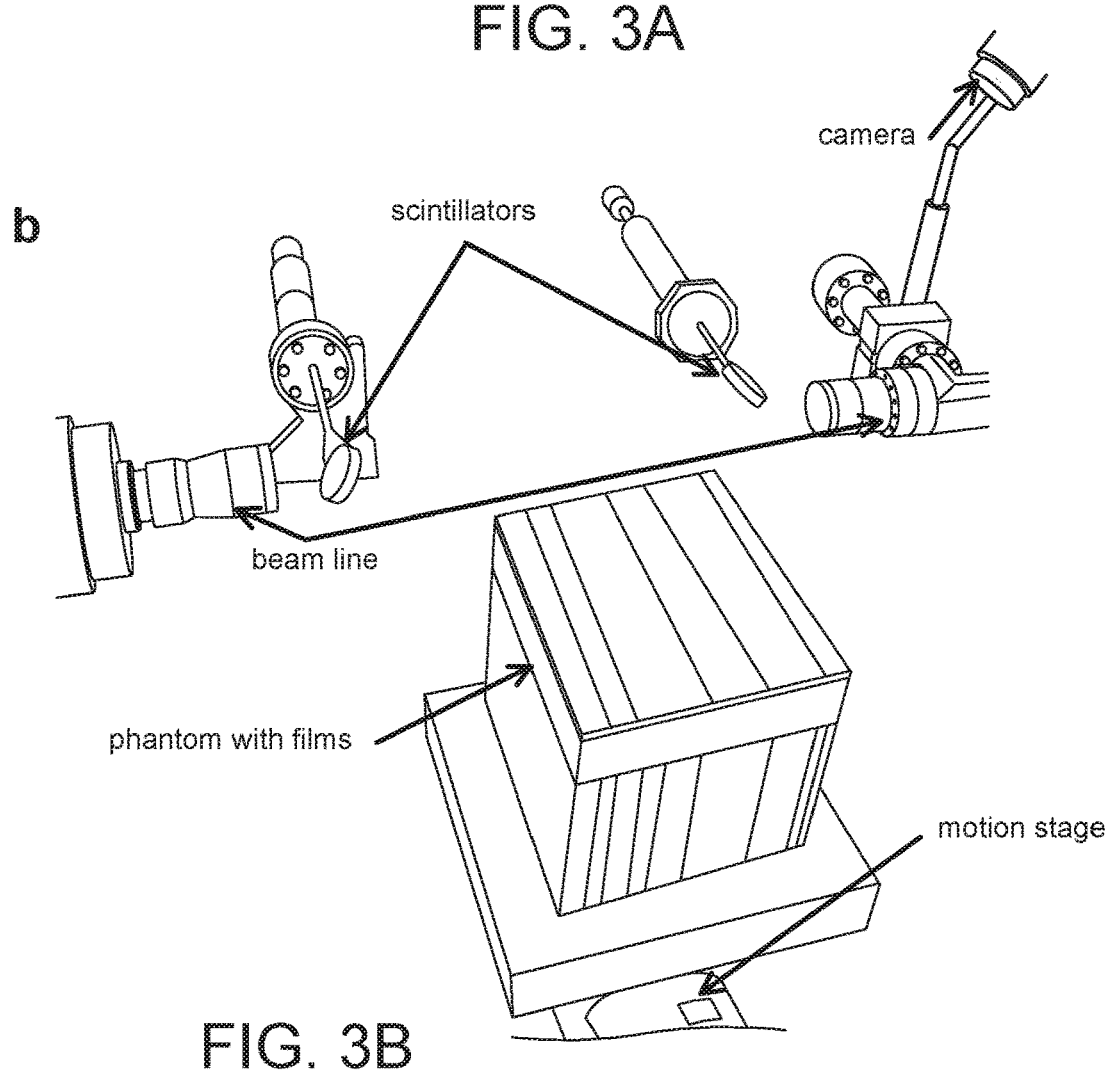
Figure 3:
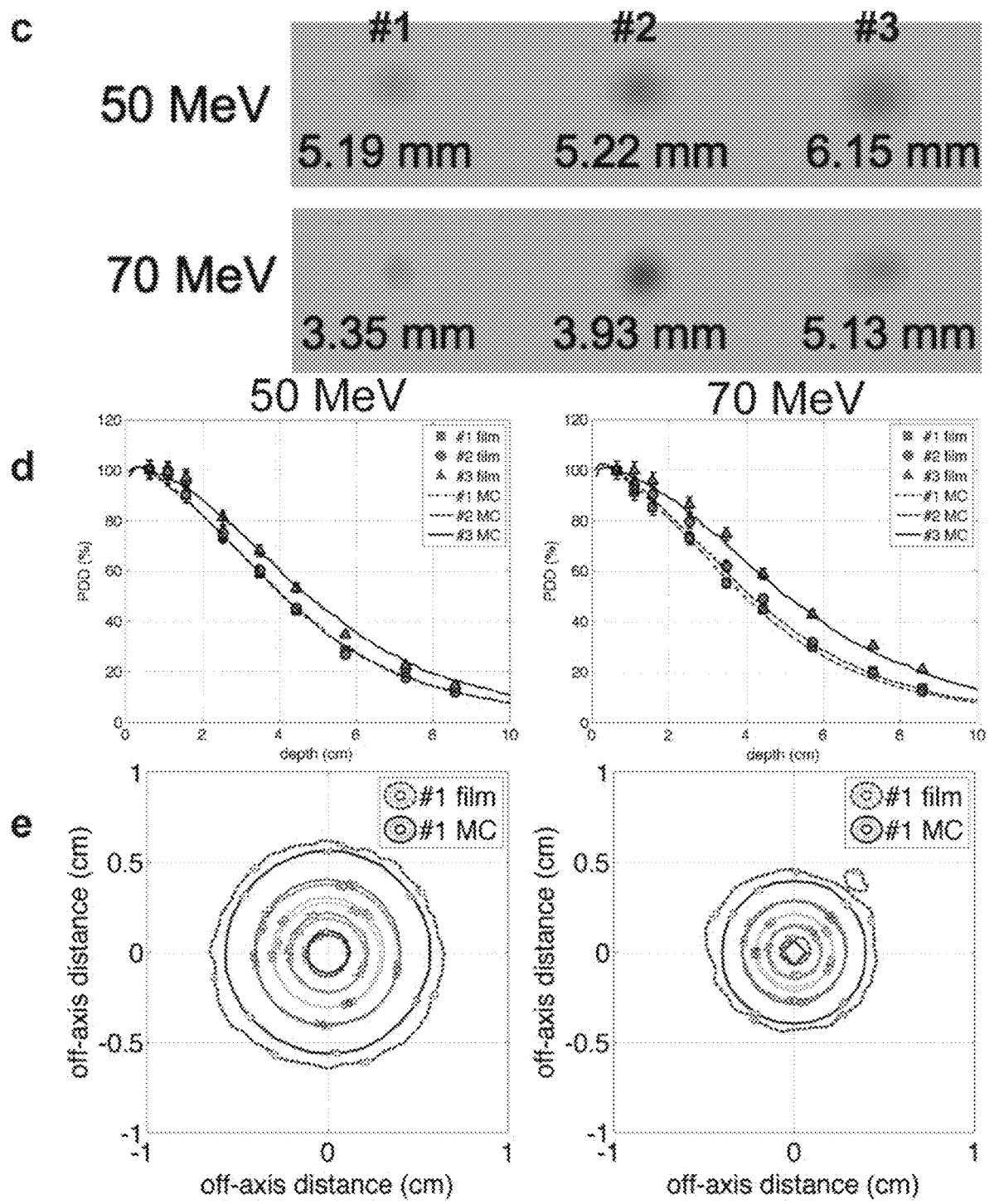

To demonstrate the accuracy of Monte Carlo calculations with VHEE beams, the inventors experimentally measured the dose distribution and depth dose profiles at the NLCTA facility at SLAC. Of note, the NLCTA employs compact high-gradient linear accelerator structures which can produce beams that are relevant to those potentially suitable for certain embodiments of the invention. The inventors assembled a dosimetry phantom by sandwiching GAFCHROMIC EBT2 films (International Specialty Products, Wayne, N.J.) between slabs of tissue equivalent polystyrene as shown in FIG. 3. FIG. 3a is a schematic and FIG. 3b is a photograph of the experimental setup for film measurements (FIG. 3c) of very high-energy electron beams at the NLCTA beam line at SLAC. Monte Carlo simulations and film measurements of percentage depth dose curves (FIG. 3d) and 2-D dose distributions taken at 6 mm depth (FIG. 3e) for 50 MeV and 70 MeV beams demonstrate a high degree of agreement between calculation and measurement.

By way of procedure and in greater detail, the phantom as shown in FIG. 3a was irradiated with 50 MeV and 70 MeV beams. Three beam sizes ranging from 3.35 to 6.15 mm were tested for each energy level. The energy was measured by a spectrometer upstream from the location of the experiment and the beam size was measured by two scintillating screens using two cameras just before and after the phantom with the phantom removed from the beam line (FIG. 3b). The films were calibrated with a clinical electron beam at 12 MeV. MC simulations have demonstrated no energy dependence of the film response at electron energies above 1 MeV. The number of particles required to irradiate the films to dose levels between 1-5 Gy to match the dynamic range of the film was determined for each beam size using MC simulations and used in the experiment. The charge was set to 30 pC/pulse corresponding to $1.9 \times 10^8$ electrons and the pulse rate was reduced to 1 Hz for easier control of the exposure. The number of pulses varied from 2 to 40 pulses depending on the beam size. The experimental and calibration films were read out in a flatbed scanner (Epson Perfection V500, Long Beach, Calif.) with 0.1 mm pixels 24 hours after irradiation (FIG. 3c) and central axis percentage depth dose (PDD) curves and 2-dimensional dose distributions at various depths were plotted. The experimental setup was simulated in MCNPX 5.0 MC code. (See Palowitz D B, MCNPX User's Manual, Version 2.7.0, 2011. available online at (http://mcnpx.lanl.gov/documents.html), incorporated herein by reference).

The simulations are compared to measurements in FIG. 3d-e. Good agreement was observed for both the PDD curves and beam profiles for 50 and 70 MeV. These preliminary results indicate that dose from VHEE beams can be measured with GAFCHROMIC films and that VHEE beams can be accurately simulated with the GEANT4 code.

In the arrangement shown in FIG. 3b, a 50-μm vacuum window made of stainless steel was used to interface the accelerator line with open air, in which the dose phantom (FIG. 2a) was placed. The stainless window was found to cause significant angular beam spreading, so that the simulations were also performed with a beryllium window which imparted less beam spreading. While a vacuum window is necessary to separate the vacuum of the accelerator beam line from the open air and the patient, significant angular spread will adversely affect beam performance and clinical accuracy. The angular spread from a thinner beryllium window was still present but it was much smaller than steel, due to beryllium's low atomic number.

b. Cross Validation of Monte Carlo Codes

Figure 4:
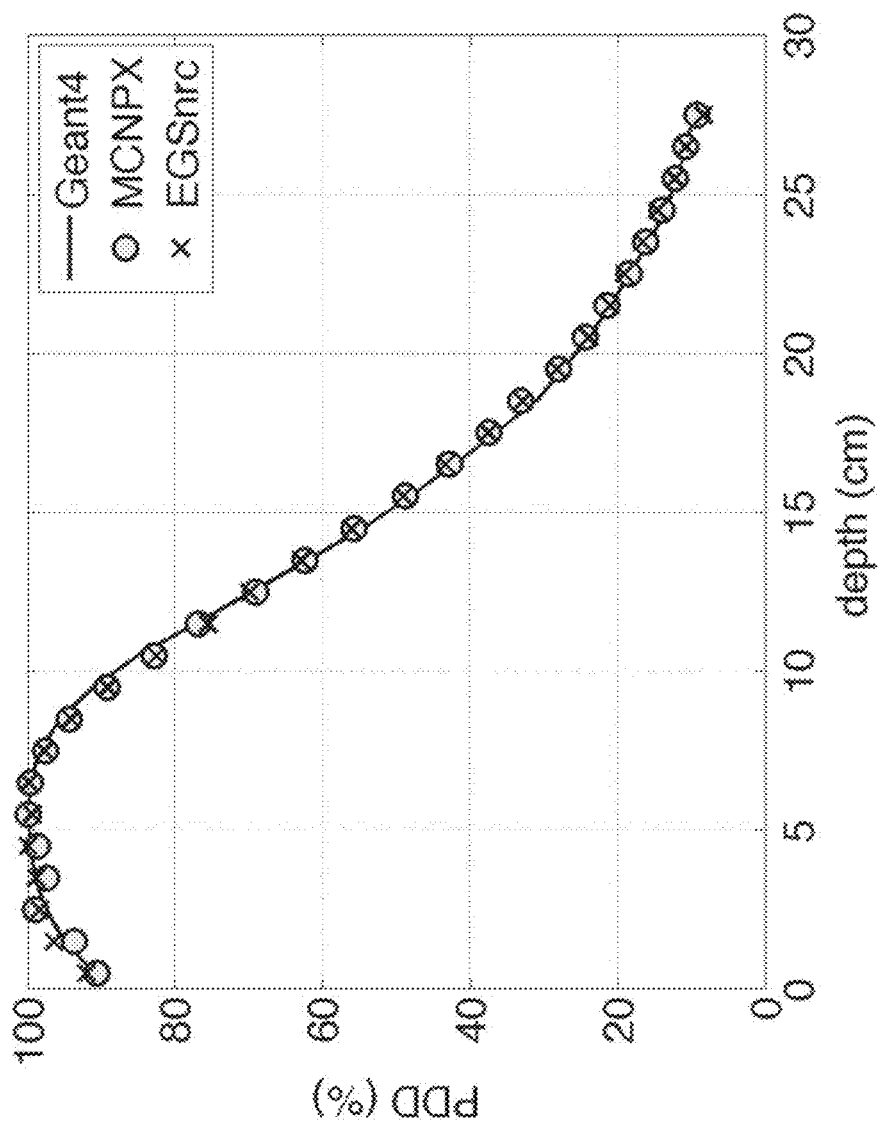
FIG. 4 shows graphic representations of percentage depth doses for a 2×2 cm 100 MeV electron beam in a water phantom, simulated using three independent Monte Carlo codes.
Figure 7:
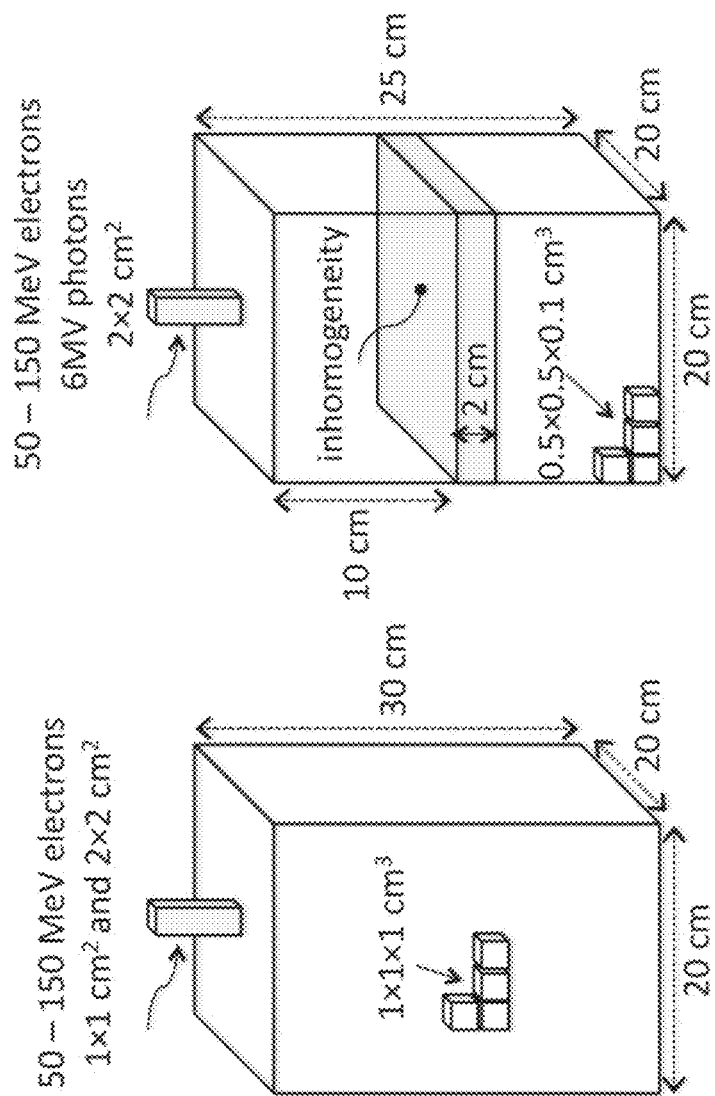
FIG. 7 shows water phantoms used in Monte Carlo simulations conducted in accordance with certain embodiments of the invention.

The inventors performed Monte Carlo simulations using three independent codes for identical geometries to determine the consistency of calculated doses. The dose deposition of a number of rectangular electron beams incident on a 20×20×30 cm water phantom (as shown in FIG. 7a) was simulated in the GEANT4, MCNPX, and EGSnrc MC codes. The simulated electron beam energies were 50, 75, 100, and 150 MeV with beam sizes of 1×1 cm and 2×2 cm. The central-axis PDDs were plotted and compared for all three MC codes. Excellent agreement was found between the codes for all of these comparisons, as shown in FIG. 4, which shows PDD for a 2×2 cm 100 MeV electron beam, simulated using the three Monte Carlo codes.

c. VHEE Tissue Interactions

Figure 5:
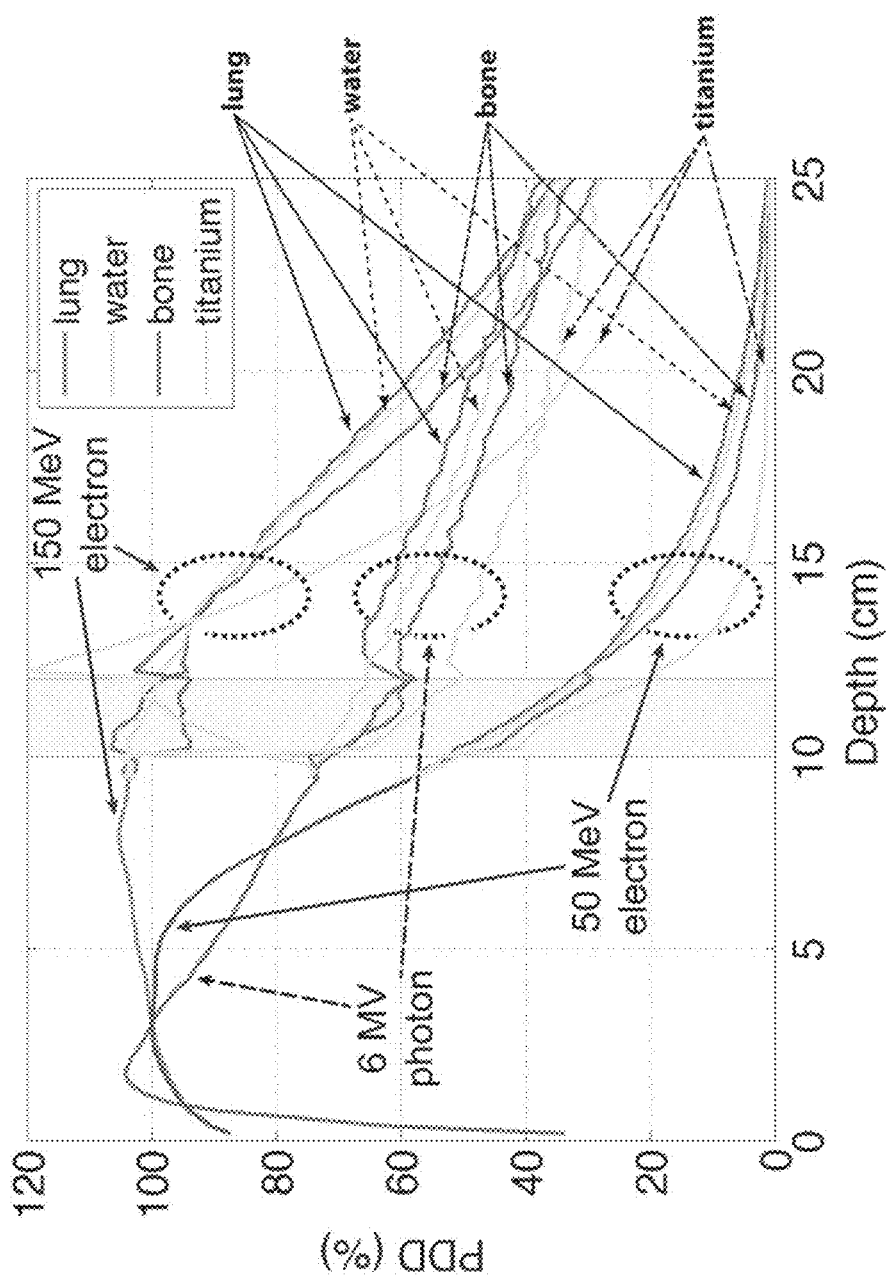
FIG. 5 shows graphic representations of percentage depth doses for 2×2 cm 50 and 150 MeV electron beams compared to 6 MV photons in a water phantom, with 2 cm thick heterogeneous tissue at 10 cm depth.

Monte Carlo simulations were performed to evaluate the impact of various tissue heterogeneities on VHEE beams relative to MV photon beams. FIG. 5 shows PDD curves for 2×2 cm 50 and 150 MeV electron beams compared to 6 MV photons in a water phantom with 2 cm thick heterogeneous tissue at 10 cm depth, normalized to identical dose at 3 cm depth. As shown in FIG. 5, the 50 and 150 MeV VHEE beams are less sensitive to tissue heterogeneity over the density range from lung tissue to titanium prosthetic implants compared to 6 MV photons.

Figure 6:
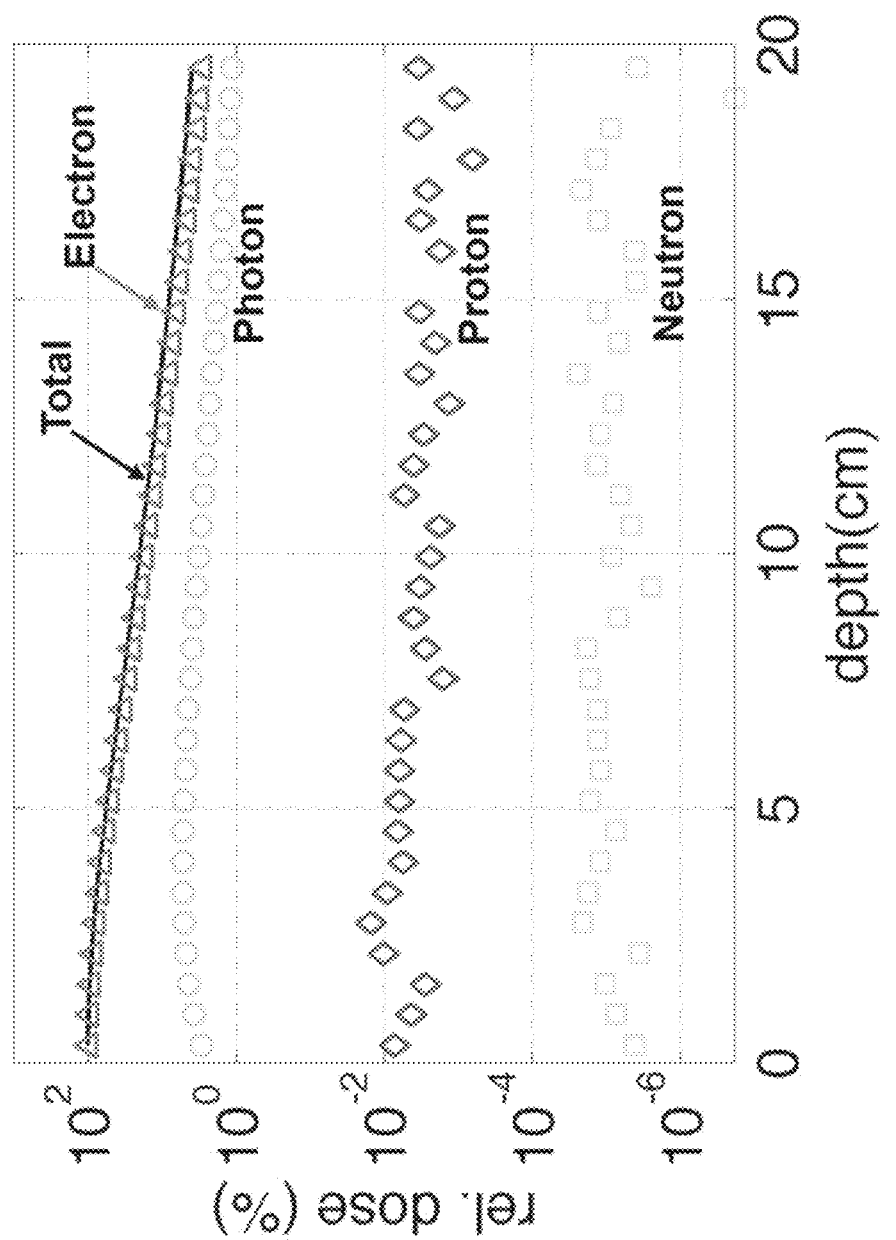
FIG. 6 shows graphic representations of relative contribution to dose from a 100 MeV electron beam vs. secondary generated particles (logarithmic scale).

Contribution of secondary particles produced by Bremsstrahlung and electronuclear interactions to the dose from VHEE beams were also analyzed. FIG. 6 shows relative contribution to dose from a 100 MeV electron beam vs. secondary generated particles (log scale). As shown in FIG. 6, for a 100 MeV electron beam, nearly all the deposited dose is due to electrons, with a minor contribution from Bremsstrahlung x-rays, and far lower dose from protons and neutrons. FIG. 6 also shows that dose from neutrons is far less than with 15-18 MV photons or high-energy protons. This holds for 50 and 70 MeV electrons as well (not shown). For a 25 Gy SABR treatment of a 2 cm diameter target, an upper limit of total body neutron dose is estimated to be 0.6 mSv based on MC simulations. This is in contrast to more than 1-2 orders of magnitude greater estimated neutron doses of 9-170 mSv for scanning beam proton therapy and 15-18 MV photon IMRT for the same clinical scenario, based on published measurements of ambient neutron doses [Schneider U, Agosteo S, Pedroni E, and Besserer J., "*Secondary neutron dose during proton therapy using spot scanning*," International Journal of Radiation Oncology Biology Physics, 2002; 53(1): 244-251. (PMID: 12007965); Howell R M, Ferenci M S, Hertel N E, Fullerton G D, Fox T, and Davis L W, "*Measurements of secondary neutron dose from 15 MV and 18 MV IMRT*," Radiation Protection Dosimetry, 2005; 115(1-4): 508-512. (PMID: 16381776) both of which are incorporated herein by this reference]. An advantage of such potential designs according to certain embodiments compared to >8 MV photon and scanning beam or passive scattering proton therapies is elimination of need for beam modifying structures prior to beam incidence on the patient, in which most neutrons are generated with existing modalities.

d. Tissue Inhomogeneities

The effect of tissue inhomogeneities on dose deposition of VHEE beams has been studied by the inventors. A 20×20×25 cm3 water phantom with 0.5×0.5×0.1 cm3 voxels and a 2-cm thick inhomogeneity placed at 10 cm depth was built (FIG. 7b). The 2-cm thick slab was consequently filled with lung with mass density ρ of 0.368 g/cm3, adipose (ρ=0.950 g/cm3), ribs (ρ=1.410 g/cm3), and cortical bone (ρ=1.920 g/cm3) tissue to assess the effect of human tissue inhomogeneities. The tissue composition was obtained from the ICRU-44 document [ICRU. Tissue substitutes in radiation dosimetry and measurement, 1989 (incorporated herein by this reference)]. Moreover, the effect of metals, such as hip prostheses, dental fillings, and surgical clips, was investigated by simulating a steel slab (ρ=8.030 g/cm3). Doses deposited by 50, 100, and 150 MeV electron beams, as well as 6 MV photon beam interacting with the inhomogeneity slab were simulated. The DOSXYZnrc code was chosen for this task due to its simplicity of use and its shortest calculation times. The statistical uncertainties in all central axis voxels were below 1%.

3. Ultra-High Gradient Accelerator Structure Design

Pluridirectional very high electron energy radiation therapy systems and processes according to various embodiments of the invention can be created with various types of electron source. There are a number of potential sources of very high-energy electrons in the range of, for example, up to about 250 MeV. A non-exhaustive list includes cyclotrons, synchrotrons, linacs (which can include more conventional designs with greater length), racetrack microtrons, dielectric wall accelerators, and laser plasma wakefield accelerator sources. Some of these are large and would need to be housed in a separate room. Some are not very mature technologies. In terms of goals of certain embodiments of the invention which can include any or all of compactness (entire system fitting within existing medical linac vaults without a separate room), power requirements, cost, repetition rates, compatibility with intensity modulation techniques described in this document, and other practical considerations, compact very high-gradient standing wave linear accelerators such as those developed at SLAC as described in the two paragraphs immediately below, or derivatives of them, may be at least a logical starting point, although other currently existing or future options should not be ruled out.

Highly efficient π-mode standing wave accelerator structures have been developed at SLAC for the project formerly known as the Next Linear Collider, a positron-electron collider at 500 GeV energy for high-energy physics research [Dolgashev V, Tantawi S, Higashi Y, and Spataro B, "*Geometric dependence of radio-frequency breakdown in normal conducting accelerating structures*," Applied Physics Letters, 2010; 97(17). (http://apl.aip.org/resource/1/applab/v97/i17/p171501_s1) incorporated herein by this reference (hereinafter sometimes "Dolgashev 2010"). Such accelerators are capable of accelerating electrons to 100 MeV within 1 meter (Id.) using an optimized accelerating waveguide powered by a 50 MW 11.4 GHz microwave generator (klystron) [Caryotakis G. Development of X-band klystron technology at SLAC. Proceedings of the 1997 Particle Accelerator Conference, 1997; 3: 2894-2898. (http://ieeexplore.ieee.org/xpls/abs_all.jsp?arnumber=752852) incorporated herein by reference]. In order to produce a practical system in terms of cost and size, optimized designs according to certain embodiments of the invention allow both economical production and high performance to minimize the treatment time while allowing maximum possible flexibility in beamlet shapes, directionality, and energy.

Furthermore, it has been shown that coupling a series of small sections of standing-wave accelerators with a distributed radiofrequency (RF) network makes it possible to design a system without any reflection to the RF source [Tantawi S G, "*rf distribution system for a set of standing-wave accelerator structures*," Physical Review Special Topics-Accelerators and Beams, 2006; 9(11) (http://prst-ab.aps.org/abstract/PRSTAB/v9/i11/e112001) incorporated herein by this reference (hereinafter, "Tantawi 2006"). Building on these developments, practical implementations of a standing-wave accelerator structure have been designed to accelerate electrons to 100 MeV within one meter. (See for example, Neilson J, Tantawi S, and Dolgashev V, "Design of RF feed system and cavities for standing-wave accelerator structure," Nuclear Instruments and Methods in Physics Research A: Accelerators, Spectrometers, Detectors and Associated Equipment, 2011; 657(1): 52-54. (hereinafter, "Neilson 2011"), available online at (http://www.sciencedirect.com/science/article/pii/S0168900211008898), incorporated herein by reference). Such accelerators can serve as a basis for or be relevant to certain embodiments of the invention.

D. Other Design Issues

1. Design Options for the Injector System

To inject the required low charge bunch into accelerators according to certain embodiments of the invention, several possibilities are available. Those include a photo-injector RF gun. Additional options can be considered to reduce the cost and size of the system, including a variety of field emitter configurations and RF thermionic guns.

2. Optimization of the RF Source by the Addition of a Pulse Compression System

RF source requirements depend ultimately, at least in part, on the accelerator design. With the optimized cavities as described above, it is projected that a 50 MW source at X-band will be sufficient for a 2 meter accelerator operating at 50 MV/m. This type of source is available at SLAC and is being commercialized by Communications & Power Industries (Palo Alto, Calif.). With the use of a pulse compression system it may be possible to either reduce the cost and sophistication of the RF source dramatically or make the accelerator structure more compact by reducing the length to 1 meter. Because the typical filling time of such a structure is about 100 ns and the RF source typically provides several us long pulses, one can use a compact pulse compressor with a high compression ratio and a power gain of about 3.5 to reduce the required RF source power to only about 14 MW, which opens the door for a variety of sources, including sources that are commercially available now, and including those that include a pulse compression system.

3. Implementation of Intensity Modulation

According to certain embodiments of the invention, which may be used with various types of accelerators in accordance with the invention, and in order to achieve highly conformal volumetric dose shaping, radiation fields from each of multiple beam directions can cover an area with varying beam intensity across the field, with the intensity patterns optimized to produce the desired 3-dimensional dose distribution when summed across all beam directions. Such intensity modulation may be produced by raster scanning individual beamlets of varying intensity across the field from each beam direction. Alternatively, it may be produced by using a 2-dimensional intensity-modulated electron pattern at the source, effectively an array of beamlets of varying intensity, and accelerate and steer the entire array to the target volume. This eliminates the need for a raster scanning mechanism at the exit of each of the beam channels, greatly simplifying the design and reducing the bulk and cost of those components, and increases the treatment delivery speed by delivering beamlets in parallel within a much smaller number of electron pulses or bunches.

II. Technologies to Facilitate Radiation Delivery in Rapid Radiation Treatments

A. Photo Cathode/Photo Electron-Gun

In accordance with certain aspects, methods and systems for rapid generation and delivery of transversely patterned electron beam to targeted tissue for rapid radiation treatment utilize a photo-electron gun. A photo-electron gun is one of various possible techniques that may be used for precise and ultrafast dose delivery using a medical electron accelerator in accordance with the present invention. The dose is produced in rapid pulses of electrons delivered to the targeted tissue from different directions, different transverse beam pattern in each direction. Each pulse has a pre-programmed transverse dose pattern such that the total 3D dose conforms to the target volume in the patient. Projecting a pre-programmed light pattern on a photocathode generates replica of this light pattern with similar transverse distribution of the electrons. This pattern or image is then accelerated through low aberration electron optics toward the targeted tissue.

According to some embodiments, the intensity modulation of the electron source may be produced by using a photocathode illuminated by a light source with the corresponding intensity pattern, in effect, an optical image. One implementation is to use a laser as the light source, and a digital light processing (DLP) micromirror array or other intensity modulating device to produce the charge image on the photocathode to be accelerated and steered. The electron beam optics can be designed to maintain the pattern with high fidelity until it reaches the target.

Figure 8:
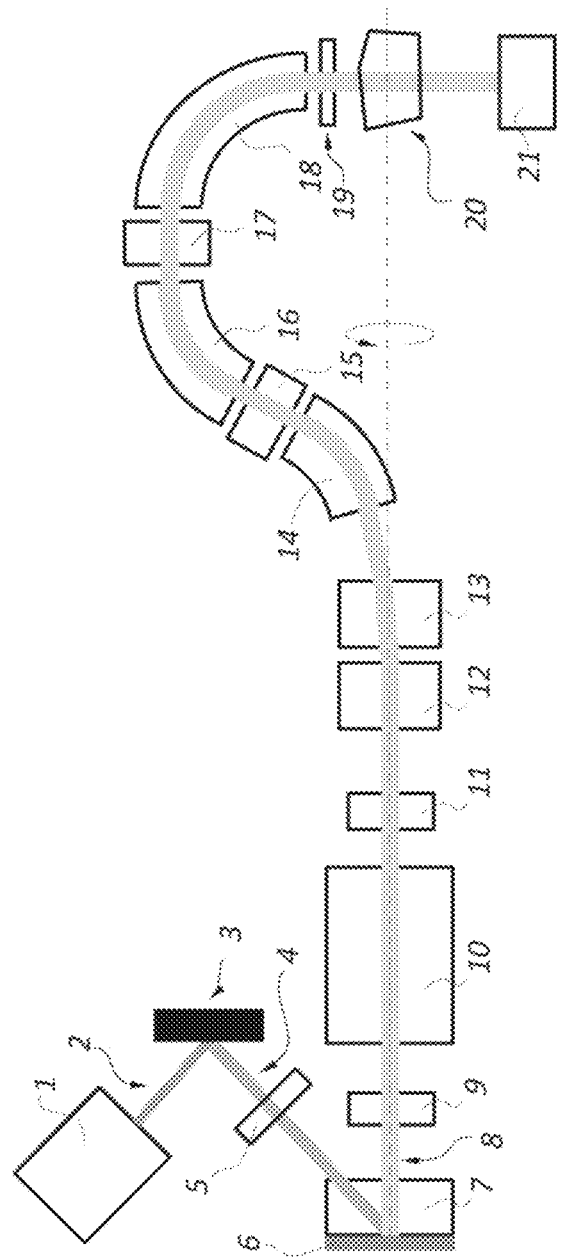
FIG. 8 schematically shows portions of a radiation treatment system with modulation of electron beam transverse profile using pulse-to-pulse modulation of injection laser beam profile impacting a photocathode of an electron injector.

According to one nonlimiting embodiment as shown in FIG. 8, a short, typically picosecond-long pulse with uniform transverse profile is generated by a laser 1. The wavelength of the laser is matched with specific photocathode material to obtain required charge and emittance. The laser pulse 2 falls on a digital-micro-mirror device 3. Pixels of this micro-mirror device are controlled by a computer and will reflect a portion of the laser pulse 4 thus creating an image that is then transferred to the photocathode (6) using precision projection optics 5. Although various types of accelerators may be used with this embodiment, high gradient pulsed devices with a few milliseconds between pulses are preferable. The computer modulates the mirror array thus creating a new image for each consequent pulse. A laser pulse with amplitude-modulated transverse profile that impacts the photocathode 6 will create an electron replica of the laser pulse transverse profile 8. The photocathode 6 is a part of photo-electron gun 7. The gun creates an electric field on the photocathode which accelerates the transverse-modulated electron beam. The gun also provides initial focusing for the electron beam. The electron beam then passes through the low-aberration focusing system 9 toward accelerator 10. The accelerator increases energy of the beam to a desired value. The electron beam then passes through focusing optics 11 toward horizontal 12 and vertical 13 fast deflectors. The deflectors are controlled by a computer and are able to send the electron beam in different directions for each consecutive accelerator pulse. The desired direction will depend on (among other things) specific realization of the gantry's beam lines, number of the beam lines and whether they are movable or not. For clarity only one gantry beam line is shown in FIG. 8. After the deflectors, the electron beam passes through bending magnets 14, 16, 18 and electron optics 15, 17 and is directed through electron-beam monitoring system 19 toward the target 20. The transversely modulated electron beam irradiates the target with required distribution of the dose. After passing through the target, the beam is sent toward beam dump 21 in order to reduce unwanted radiation exposure of the target.

The concept of conversion of an optical intensity pattern into a radiation intensity pattern within a patient is considered to be unique, and also uniquely applicable to electron beam therapy in accordance with embodiments of the invention as opposed, for example, to photon or proton or other particle therapies. In certain aspects, the light-pulse generation could be based on laser, light-emitting diode, or various other light sources with power, wavelength, and pulse length optimized to produce sufficient electron charge and initial emittance from a specific photocathode material.

B. Array of Accelerating Structures

1. Overview:

One way to increase the speed of radiation delivery is to direct beams to the targeted tissue from multiple directions in rapid succession or nearly simultaneously through an array of accelerating structures rather than by mechanically rotating or moving a single linac source around the patient. This configuration is generally not practical if the typical high-power radiofrequency (RF) power source (eg, a klystron or magnetron) must be replicated multiple (N) times, requiring N high-power sources for N accelerator structures. These challenges can be overcome by use of the following innovations, illustrated in the embodiments of FIGS. 10A-10B.

In accordance with certain embodiments of the invention, one or more RF power supplies (ideally compact), including low voltage multi-beam klystrons, provide efficient radiofrequency power that is distributed to an array of electron accelerating structures through a multi-port phased array microwave network. Typically, the array of accelerating structures is configured to accelerate electrons, although in some embodiments the structures may be adapted to accelerate other particles (e.g. protons, ions). These technologies can be used to apply radiation therapy using conventional therapeutic electron beam energies (1-20 MeV) with or without conversion to high-energy photons (x-rays), as well as very high-energy electrons (up to 250 MeV). When treating with photons, scanning of an electron beam across a stationary bremsstrahlung target and collimator array eliminates the need for mechanical collimator motion. An electron gun that produces a two-dimensional transverse intensity-modulated electron beam and beam optics to propagate this pattern through the accelerator to the target in the patient can be used to replace raster-scanning mechanisms. The system integrates imaging of sufficient speed and quality to permit real-time treatment planning and position verification and treatment delivery all within the specified time frame or alternatively may be used to apply a predetermined treatment plan using real-time imaging. Variations of the design are discussed in further detail below.

Figure 9A:
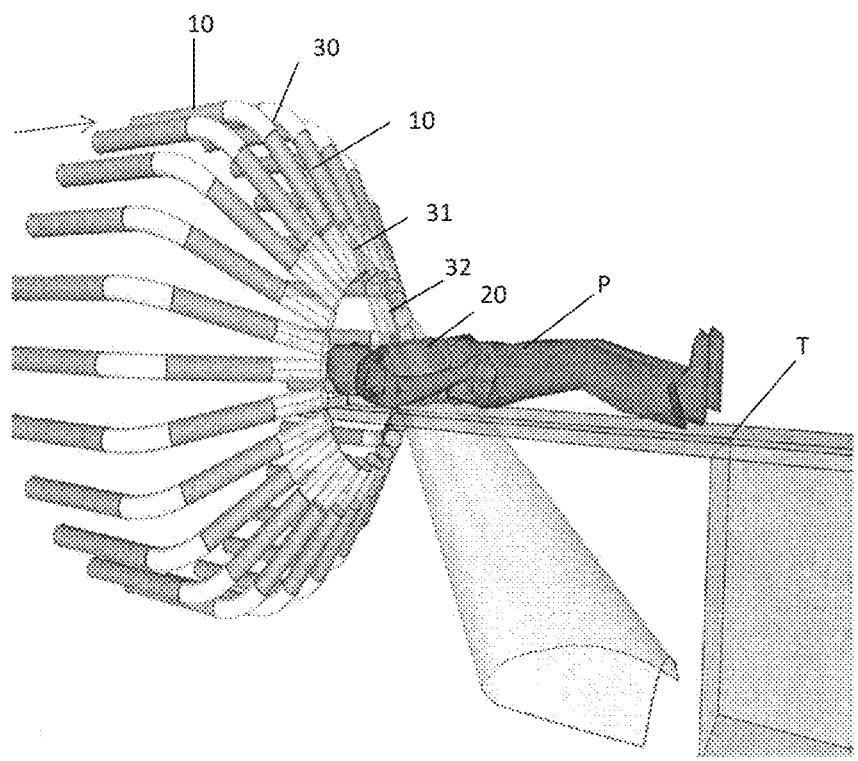
FIGS. 9A-9B illustrate a rapid radiation delivery system utilizing an array of accelerating structures.
Figure 9B:
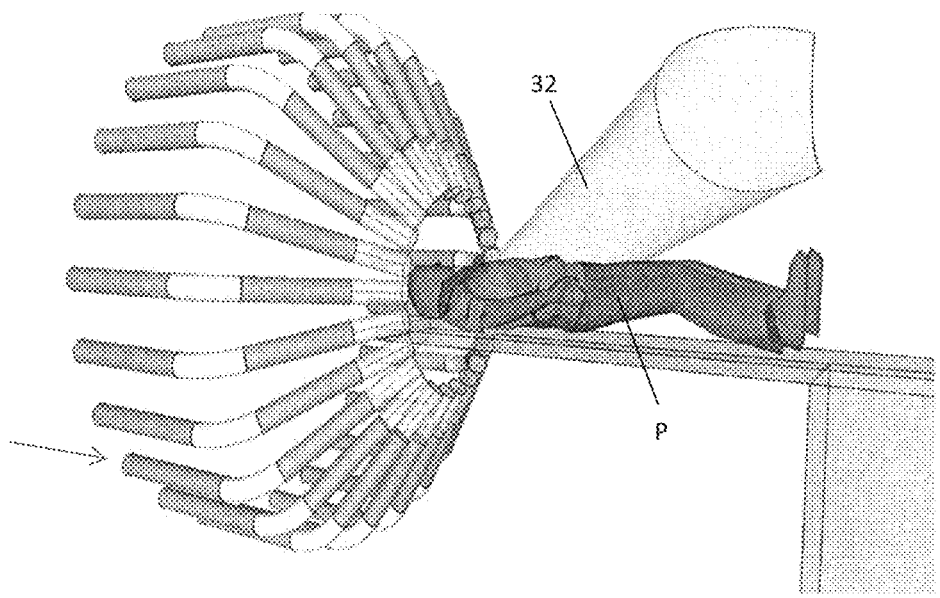

FIGS. 9A-9B shows one possible multi-beam geometry of an array of accelerating structures 100, each of which shows the components of an individual beamline. In this example, the treatment particle beam extends through a first accelerating structure 10, through a bending structure 30 that directs the accelerating particle beam towards the targeted tissue, and then through a second accelerating structure 10, through a treatment head 31 to form the treatment beam 32 before delivery to the targeted tissue 20 of the patient P disposed on the surgical table T of the system. In some embodiments, the treatment head may include any number of beam shaping or collimation devices or a beam monitoring or verification device to ensure the beam or an associated pattern is within acceptable parameters before delivery to the targeted tissue.

In certain embodiments, the array includes multiple accelerating structures, such as two or more accelerating structures directed towards the same target so as to allow a treatment beam to be directed to the targeted tissue from more than one direction. Typically, the array includes many accelerating structures, such as four or more, often between 15 and 35 accelerating structures. In the example shown in FIGS. 9A-9B, the array includes a configuration of 25 beamlines around the patient. In one aspect, the beamlines are activated rapidly in sequence to direct beams to the patient target zone from multiple different directions as can be seen in FIGS. 9A-9B.

It is appreciated that the above described features relating to an array of accelerating structures may be used in various other radiation treatment systems, including those with radiation delivery time scales greater than the reduced delivery times associated with rapid radiation treatments.

2. Power Distribution to Multiple Accelerator Structures Through a Phased Array

In accordance with the present invention, a power distribution system for powering multiple accelerator structures may use a number (N) of relatively low-power sources such that their total power is directed to any given accelerator structure at a time in rapid succession. The RF may be directed appropriately through source phasing into each accelerator transmitting a treatment beam such that each accelerator feed can receive a peak power up to N times that of a single source. This approach utilizes multiple lower power sources to provides sufficiently high power (higher than each individual power source could provide) to operate each accelerating structure. Lower power sources operate at lower voltages and hence are less expensive and more compact. Generally these sources are either amplifier type sources (e.g., klystrons) or phase locked oscillators (e.g., externally phase locked magnetrons). The RF power sources could include linear devices and/or cross field devices or solid state devices.

Figures 10A, 10B:
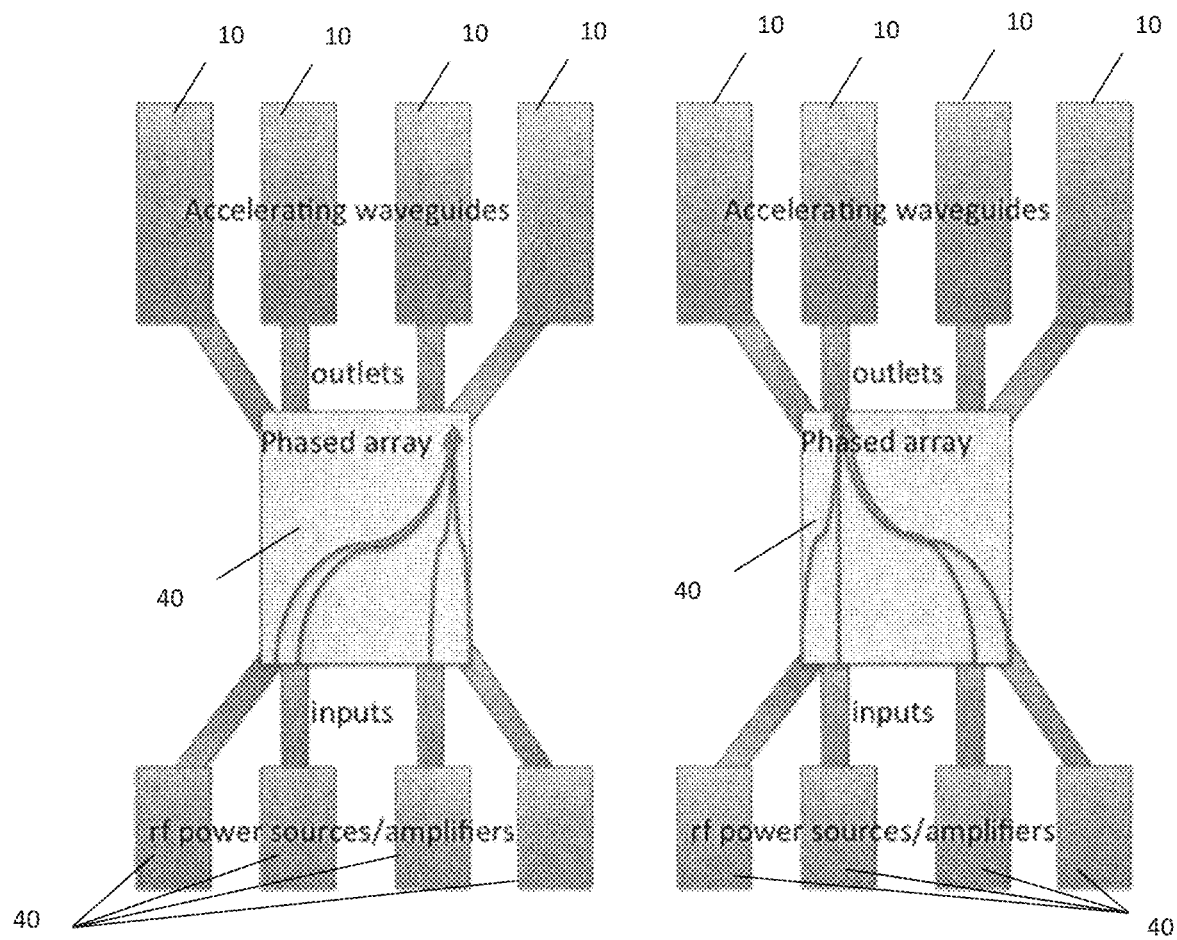
FIGS. 10A-10B depict schematics of an array of RF power sources for powering an array of accelerating structures such as those shown in FIGS. 9A-9B.

In one aspect, the inputs from the N low power sources are fed into an N×N passive microwave network, an example of which is illustrated schematically in FIGS. 10A-10B. This network has a scattering matrix representation that isolates the N input ports from each other, and because of the design symmetry of such a device, it isolates the N output ports from each other. The coupling between each input port and each output port, by design, is made equal, so that in accordance with energy conservation, it has amplitude of $1/N^{1/2}$. If these conditions are satisfied, then due to the unitarity of the lossless scattering matrix, the device is matched without reflection to the source and is forced to act as discrete phased array: that is, for equal amplitudes at the input ports, there exists a set of phases that direct the output to only one output port, and one can select this output port at will by varying appropriately the input phases.

FIGS. 10A-10B illustrate a schematic of an array of RF power sources/amplifiers in accordance with embodiments of the invention. For illustrative purposes the array includes four sources, although it is appreciated that the array is not limited to a certain number sources. The number of sources used may relate to the number of accelerators within a given array or the particular power requirements of a given system. For example, in some embodiments, the system includes between two and 49 accelerators in the array such that an associated RF power distribution system may have a corresponding number of RF sources. The phased array is capable of directing pulsed RF from multiple inputs (four inputs in this example) to any of a plurality of outputs (four outputs in this example). As shown in the example of FIG. 10A, the RF power can be shifted to the right-most accelerator and through source phase shifting, the RF power can be directed to other another accelerator, for example to the second-from-left accelerator.

Advantageously, such a scattering matrix is very forgiving in terms of errors to the input signal. If the amplitudes are not exactly equal or the phases are slightly off, the majority of the power will still be collected into the desired port and an error signal will appear in other ports. The amplitude of the error signal is relatively small and is degraded by a value of 1/N, so that the power appearing due to difference in amplitudes in the input port will be proportional to that difference times $1/N^2$, typically small enough to prevent the accelerator attached to that port from providing any radiation.

In one aspect, a typical realization of this device for the case of N=2 is the 3 dB hybrid according to various implementations, including the 4-port magic tee and variety of 3 dB directional couplers. From this basic building block, one can synthesize this network for any other values of N. For example, four of such 3 dB hybrids can be connected together to form a super-hybrid with 4 inputs and 4 outputs. Two of the 3 dB hybrids will have 4 inputs and four outputs. At any given state of inputs, one of the outputs from each input 3 dB hybrid can be selected. Then, the output hybrids with one input connected to one of the outputs of the input hybrid will select the final port where all the power would appear.

In another aspect, the above described method of synthesis can become cumbersome as N is increased. To simplify this network, overmolded structures can be used to synthesize directly an N=4 superhybrid. For example, eight such devices connected together can lead to an implementation of an N=16 network. This approach can be further understood by referring to IEEE Microwave Guide Wave Lett 10(12): 520, Nantista and Tantawi, the full disclosure of which is incorporated herein by reference in its entirety.

In certain aspects, the power distribution in the embodiments described above allow the source phasing to be achieved rapidly, significantly greater than in conventional radiation treatments, so as to allow extremely rapid delivery (e.g. rapidly sequential or near instantaneous) of radiation to the target tissue from differing accelerating structures within any of the time-scales described herein, preferably within 1 second or less.

The following represent example variations of the above described features in accordance with embodiments of the invention:

a. The power from multiple lower-power RF sources can be distributed to provide very high power in rapid sequence to multiple accelerating structures through a phased array network;

b. The power from multiple lower-power RF sources can be combined to provide very high power to a single accelerating structure through a phased array network;

c. The power from a single very high-power RF source can be divided among multiple accelerating structures through a phased array network; and d. Rather than multiple separate RF power sources, very high RF power could be provided by a multibeam klystron, which is essentially several klystrons within one vacuum envelope to reduce the cost, that would feed RF into the multiple inputs of the phased array, as is described in more detail below. These configurations allow for greater compactness and greater radiation delivery speed than existing technologies.

It is further appreciated that the above described power distribution variations described above may be used in various other radiation treatment systems, including those with radiation delivery time scales greater than the reduced delivery times associated with rapid radiation treatments.

3. overmolded Multi-Beam Compact Klystron

Figure 11A:
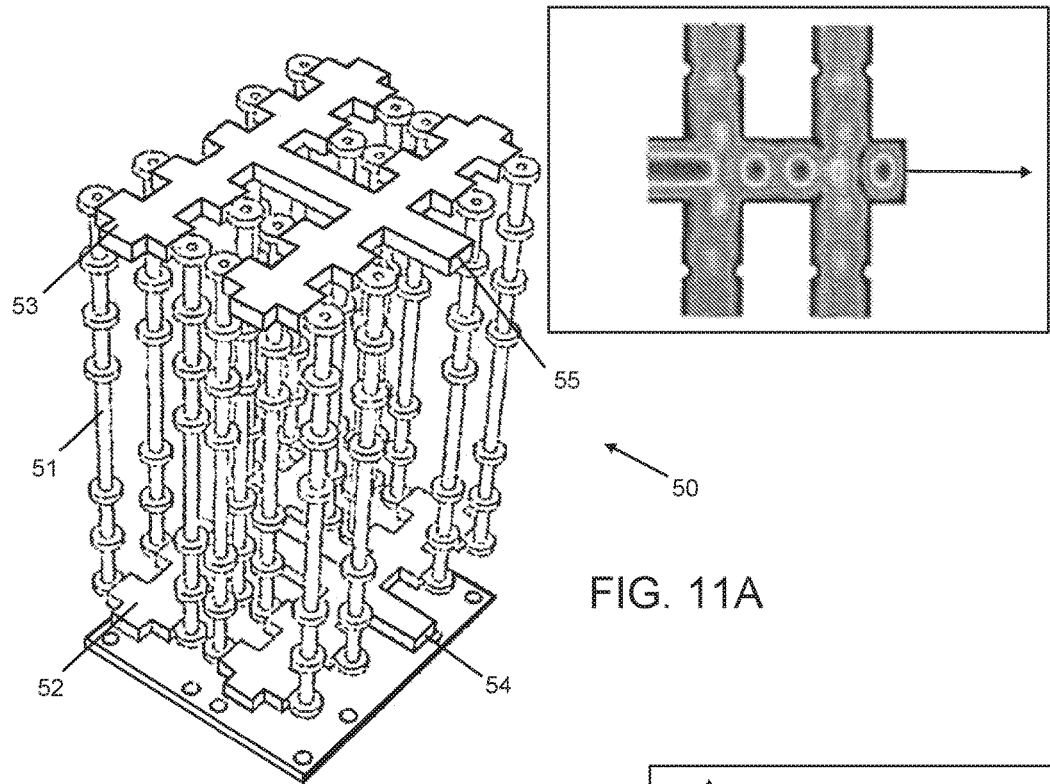
FIGS. 11A-11C illustrate a multi-beam compact klystron configurations such as may be used in a rapid radiation delivery system.
Figure 11B:
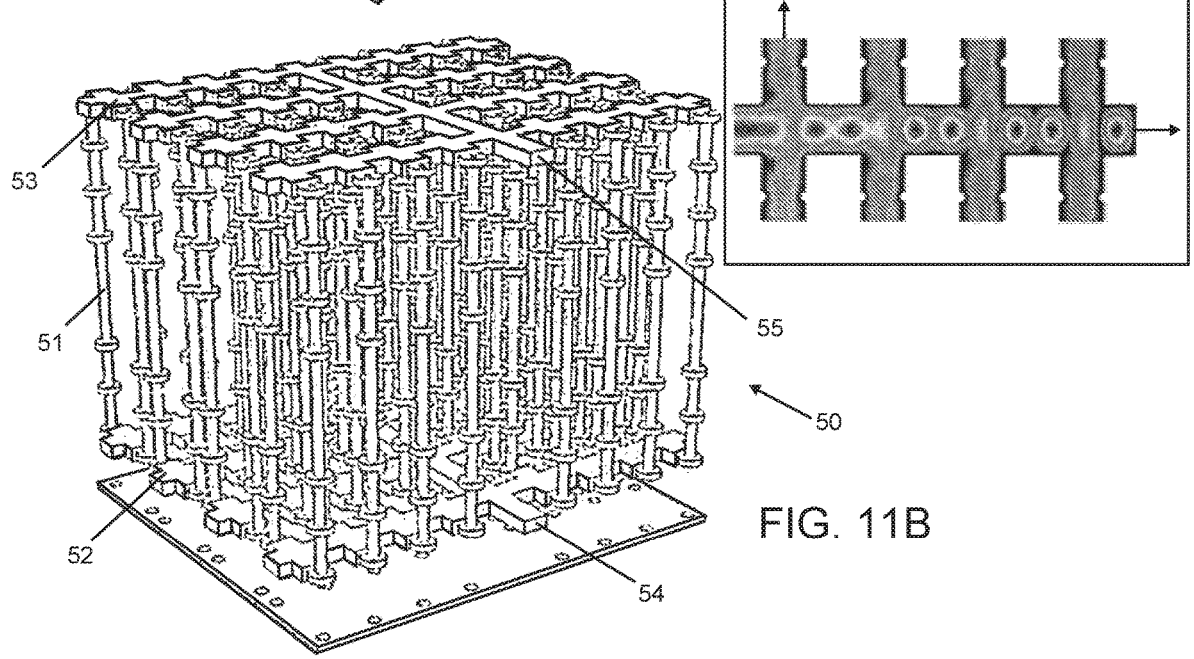

In accordance aspects of the invention, embodiments may utilize a multibeam device, in which a large number of beams are combined together while preserving the advantages of single moded system and at the same time allow for the size of the system to be large compared to the wavelength, that is, the system is highly overmolded. This multibeam device is referred to as a multi-beam klystron. This configuration can be realized by utilizing RF distribution systems and overmolded high power RF systems. This multi-beam klystron is based on a set of combining/splitting waveguide networks as shown in FIGS. 11A-11B. For example, the power can be combined from 4 different inputs with a device that has one input/output and two two-output ports symmetrical around the waveguide axis, which may be referred to as a n=2 configuration. In the example shown in FIG. 11A, a multibeam device includes a 16 six cavity klystrons, each individual klyston 51 having a drift tube with six cavities extending between an input combiner 52 (acting as an input buncher grid) and the output combiner 53 (acting as a catcher cavity grid). The input combiner may have a single input 54 and the output combiner, a single output 55, although it is appreciated that the number of inputs and outputs may vary in other embodiments.

In one aspect, such a configuration provides a multi-beam system with a highly overmolded structure, which allows for a more compact configuration. The number of beams is $(2N)^2$, where N is the division ratio for a single splitter. The output degrades a $(1-M/(2N)^2)^2$, where M is the number of Off beams. Focusing may be performed along the drift tube by electromagnets, or preferably by permanent periodic magnets (PPM) such that no electromagnets are required, which allows for operation at lower voltages, such as 100 kV or less; a simplified gun structure; no oil is needed since high voltage is avoided, an efficient, inexpensive modulator; and the possibility of using gridded cathodes.

Figure 11C:
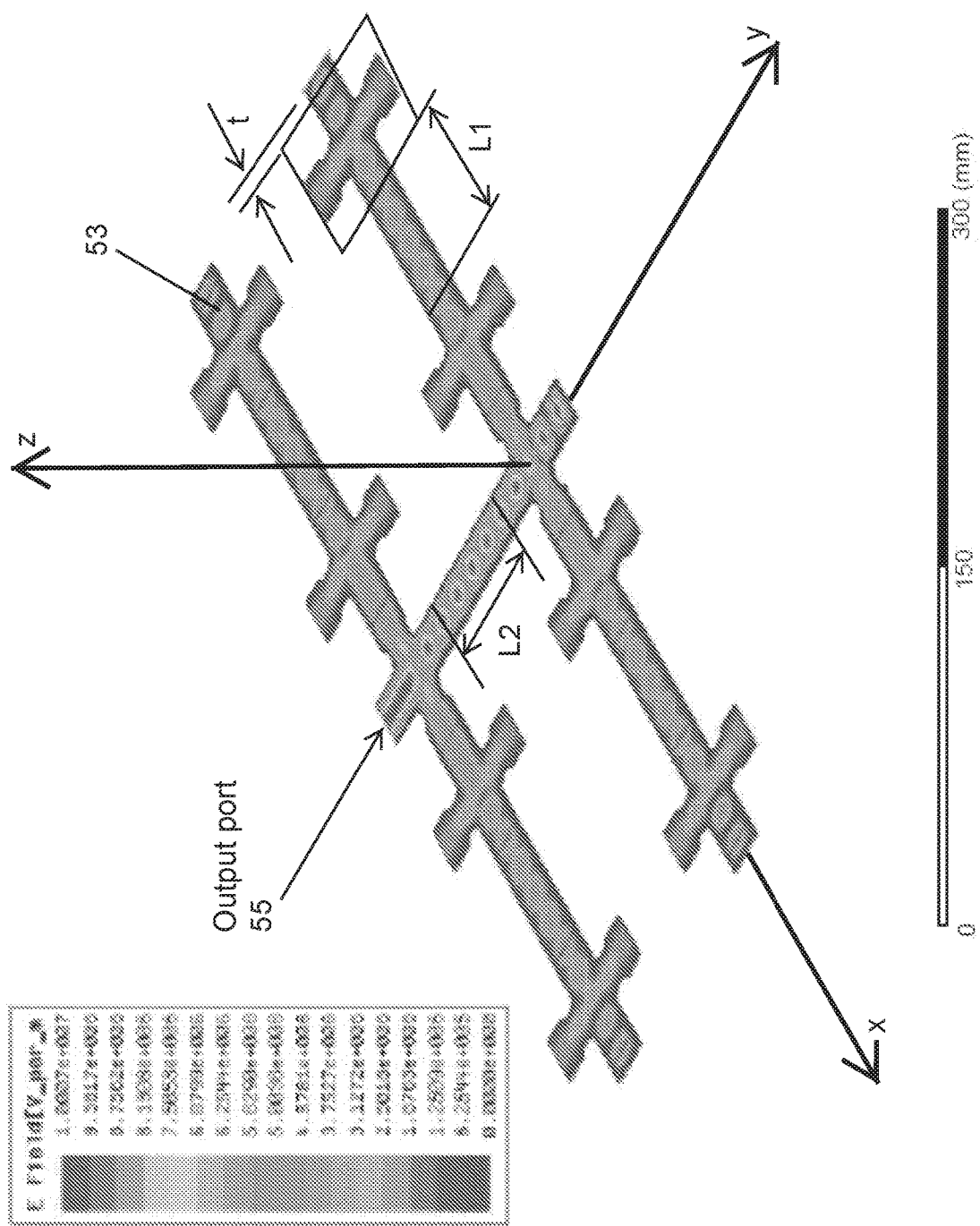

In certain aspects, utilizing one topology of these devices the input and output cavities of a set of $(2n)^2$ klystrons can be combined into one single device as shown in FIGS. 11A and 11C, which shows a combination scheme for 16 klystrons by utilizing the n=2 configuration. Referring to the dimensions illustrated in FIG. 11C, L1 can be any length according to the relationship, L1=n*0.630845", where n is an integer, adjusted to fit the klystrons, which in this example is n=4. L2 can be any length according to the relationship L2=m*0.630845", where m is an integer, adjusted to fit the klystrons, which in this example is m=4. In this example, t=0.315423". Note that at the ports, the wave is always traveling such that there are no nodes. The power is equally distributed at each portion from the output port. In this example, all the ports have a 0.9" width. The height can be chosen to simplify coupling to the cavities. However, at 6 MW and at 0.2" height the maximum field is 10 MV/m. Since it is preferable not to exceed this field, the height should not go below 0.2" for the output combiner. For the input combiner, the height may be chosen to be anything convenient, although it should be checked for attenuation if it is too small.

The optimal design of the manifold junction, which is repeated, to achieve a device that has $(2n)^2+1$ ports, $(2n)^2$ inputs/outputs plus one port as a combined output/input, can achieve a minimal standing wave within the manifold waveguide. To this end, the single junction which has a 4-port configuration as shown in FIG. 11C and labeled as a single unit, should have a very specific scattering matrix representation. By taking into account the symmetry around the waveguide axis, the reduced junction is a three port network. The representation that minimizes the standing-wave, and hence the field amplitudes and the losses within the manifold, is given by:

$$S = \begin{pmatrix} \frac{1}{-1-2n} & -1+\frac{1}{1+2n} & -\frac{2e^{i\sigma}\sqrt{n}}{1+2n} \\ -1+\frac{1}{1+2n} & \frac{1}{-1-2n} & \frac{2e^{i\sigma}\sqrt{n}}{1+2n} \\ -\frac{2e^{i\sigma}\sqrt{n}}{1+2n} & \frac{2e^{i\sigma}\sqrt{n}}{1+2n} & e^{2i\sigma}\left(-1+\frac{2}{1+2n}\right) \end{pmatrix},$$

where $\sigma$ is an arbitrary parameter to account for the arbitrary length associated with the input/output port for one of the n elements that are being combined. Note that this matrix is unitary and symmetrical and hence it respect energy conservation and reciprocity; i.e., it is always possible to find a physical realization for such a matrix. Once one unit has been designed one can combine in series a set of them to achieve a 2n combiner. In the example shown in FIG. 11C, that combiner is 4×1 combiner, for which one end has to be terminated by a short circuit at a distance $$t = \frac{\lambda_g}{4},$$

where $\lambda_g$ is the guided wavelength of the manifold waveguide. Furthermore the distance between the every two ports and the neighboring two ports connected in series can be any integer number of $$\frac{\lambda_g}{2},$$

thus allowing for this combiner to have a great flexibility to accommodate the physical sizes and features of the klystrons being combined together. Once a 2n×1 combiner have been realized, a set of 2n combiners can be combined using the same architecture of the original combiner to yield the $(2n)^2 \times 1$ combiner. The resultant system has a similar distance between every input/output to the combined output/input. Such a matrix can be implemented and realized as shown in the simulations presented in FIG. 11C.

Such a configuration allows for a resultant system that is extremely compact. FIG. 11A depicts a system that operates at 9.3 GHz, and the dimensions of the system for the case of 16 devices is about 18"×18". For a device that produces ~5 MW with about 60% efficiency, each of the beams will have 8 Amps and the system voltage is about 64 kV.

In these embodiments, each beam in this case will be separately guided by a permanent periodic magnets (PPM) system. The low current density will allow the cathodes to be flat with no or little beam compression. The low voltage of the system will allow high efficiency low cost modulators. Furthermore, the low voltages might allow the use of gridded guns, which would simplify the modulators even more.

In accordance with such embodiments, the system can be expanded to higher number of beam such as shown in FIG. 11B, which shows a system with 64 beams utilizing an n=4 combining network. In this case the power is increased to more than 50 MW. These aspects allow these configurations to achieve maximum beam density, for compactness, and a reduced amount of junctions between each cavity to the output waveguide.

Advantages of this design include its compactness and radiation delivery speed compared to existing technologies.

The array of RF sources/amplifiers coupled with a phased array that feeds the power into the each accelerator, reduces the power requirements of each power source/amplifier thus renders the entire system more compact compared to existing technologies. Through the speed of source phasing the RF power into each accelerator, much greater radiation speeds can be achieved.

While the functionality of each individual component has been described, the compactness of this design is particularly advantageous. This compactness is achieved by combining the power from multiple relatively low-power RF sources/amplifiers or any cross field devices and distributing them through a phased array into a spatially separated array of accelerators. Although the combined power fed into each accelerator through source phasing via the phased array is high, the power requirements for the individual sources/amplifiers can be low, which results in greatly enhanced compactness and cost reduction.

Figure 12A:
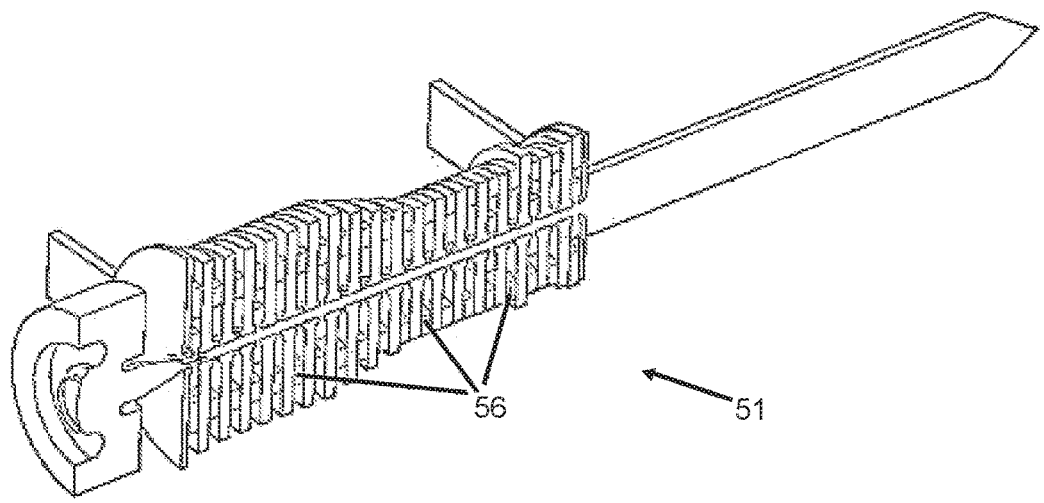
FIGS. 12A and 12B illustrate an example klystron and multi-klystron device, in accordance with aspects of the invention.
Figure 12B:
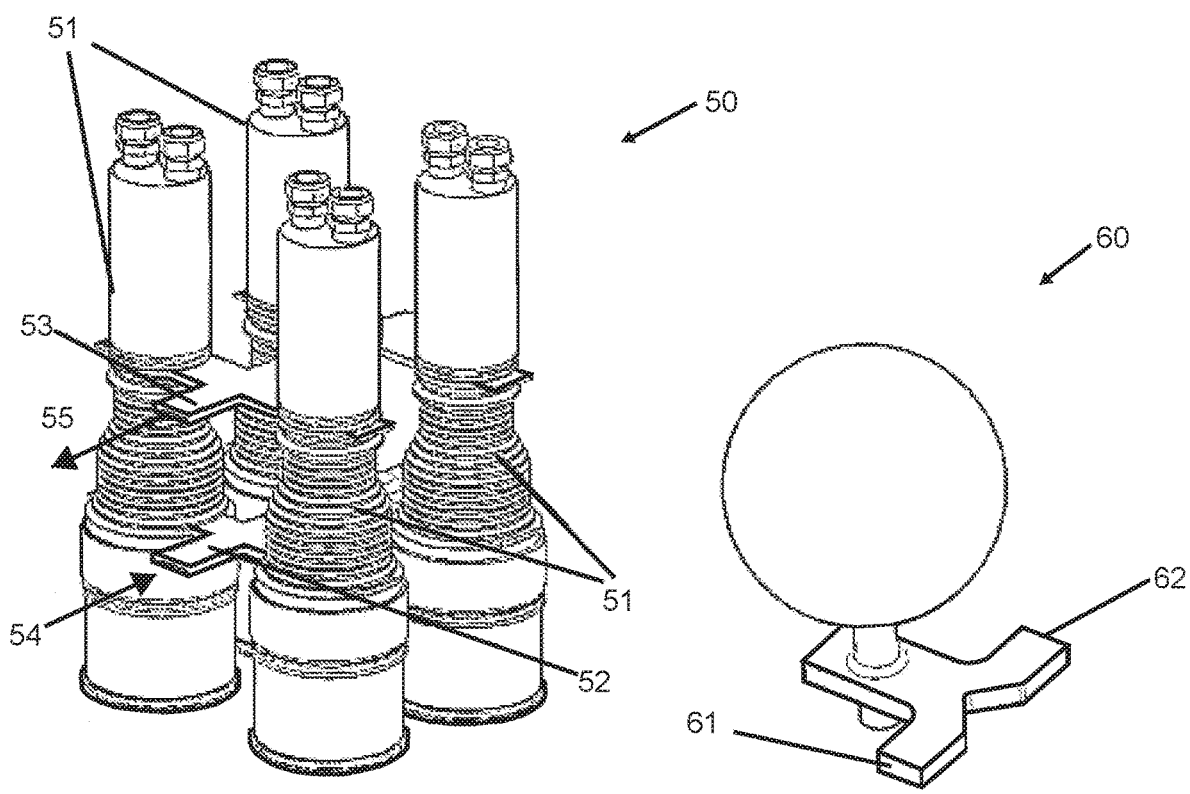
Figure 12C:
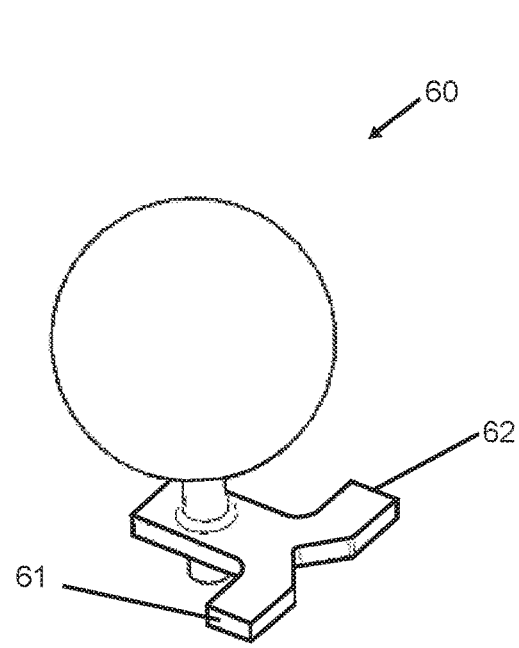
FIG. 12C illustrates an example pulse compression device for use in an RF power distribution system in accordance with aspects of the invention.

The use and advantages of the above described components within a treatment system can be further understood by reference to FIGS. 12A-14C. FIG. 12A illustrates a cutaway of a single individual klystron 51 having permanent magnets 56 for use in focusing of the beam travelling along the drift tube of the klystron. FIG. 12B illustrates a multi-beam klystron 50 with four individual klystrons 51, such as those depicted in FIG. 12A. While FIG. 12B illustrates a multi-beam klystron device with four klystrons, various other combinations may be realized in accordance with the invention, for example multi-beam klystron devices with 16 individual klystrons, such as that depicted in FIG. 11A. FIG. 12C illustrates a pulse compressor 60 having an output 62 and an input 61 for coupling with the output 55 of the multi-beam klystron device for increasing the peak power of the RF output from the multi-beam klystron. The output 62 of the pulse compressor may be coupled with an input of a phased array along with multiple other multi-beam klystrons attached to the phased array in the same manner so that that the total RF power from can be selectively directed to a select RF output of the phase array for powering an accelerator of the array.

FIGS. 13A-13B illustrate an RF phase array distribution system, having 16 RF inputs (i) and 16 RF outputs (o). FIG. 13A illustrates the housing defining the RF waveguide path with the inputs and outputs labeled and FIG. 13B illustrates the RF phase array as it would likely appear when fabricated. In one aspect, the phase array is compact, multi-port passive waveguide network which allows RF power from multiple (16) amplifier sources to be combined into any of 20 an equal number (16) of output ports through control of their relative phases. This compact 32-port waveguide circuit presents an efficient means of combining high power RF from 16 sources into any of 16 outputs and instantly switching between them by drive phase manipulation. In another aspect, the invention can also be used in reverse as a matched 16-way splitter.

Embodiments of the invention include two novel waveguide component configurations with 32 ports, 16 input and 16 output. The networks are symmetric. At the design frequency, each of the input ports is isolated from all of the others and equally coupled, with varying phase, to each of the output ports. These waveguide networks, composed solely of volume enclosed by metal walls, need no active components, dielectrics, ferrites, or any other materials.

Both the geometric arrangements and various unique component features of these networks represent novel advances in waveguide circuitry. The device may be used, for example, in medical applications where it allows multi-angle irradiation of tumors on a time scale fast compared to bodily movements—thus increasing accuracy and effectiveness while limiting collateral tissue damage—without the unrealistic expense of a 16 times higher power individual RF source for each linac. The device allows the use of smaller RF amplifiers than otherwise required and, more significantly, to allow the direction of power to several (16) destinations in quick succession by means of applied drive signal phase patterns. By analogy to radars, the phase array may be referred to as a "waveguide phased array".

One important application is for sequentially powering a set of medical linacs arranged around a patient to provide fast multi-angle radiation therapy without a turning gantry. For example, embodiments of the invention may be used in systems such as that disclosed in U.S. Pat. No. 8,618,521, which is incorporated herein by reference. Other uses are conceivable in areas such as industry and materials detection. With loads on all but one output port, they can be used simply as matched multi-source combiners, or in reverse as 16-way splitters.

In some embodiments, the waveguide circuits could be modified to have fewer ports (e.g. 8 by 8) or perhaps more ports. In addition, sub-components of alternate design could be substituted. In one aspect, a method implemented by a high power RF waveguide device may include steps of: receiving RF signals through 2n input ports, where n=2, 3, or 4, switching the received RF signals from the 2n input ports to 2n output ports using drive; performing phase manipulation by controlling relative phases of the RF signals; and transmitting by the high-power RF waveguide device RF output signals through 2n input ports.

In one aspect, the functionality of these networks can be realized in a 2 by 2 implementation (2 inputs and 2 outputs) with a simple 4-port 3-dB hybrid. Straightforwardly extending it to 4 by 4, 8 by 8 and 16 by 16 leads to increasingly complicated and extensive layouts, requiring many bends and waveguide runs to connect component ports. While embodiments of the phase array are expected to be particularly useful for high-tech medical systems for radiation therapy, it may also be useful for various other applications as well requiring high power, many-port RF combining, phased directing, or splitting. These applications might be in areas such as science, industrial processes and defense.

Figure 14A:
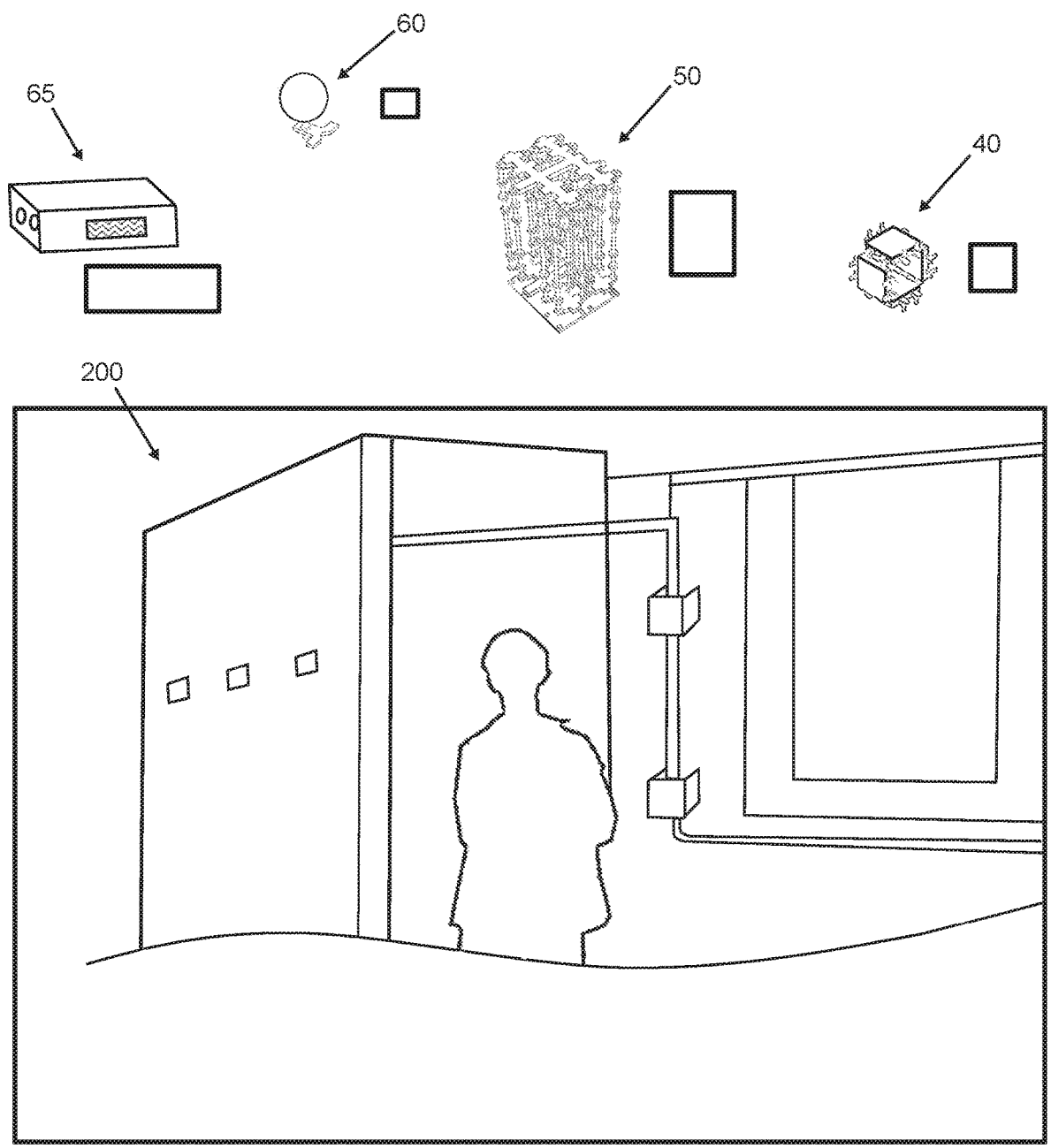
FIG. 14A depicts an approximation of relative sizes between various components of the an example power distribution system and a conventional RF power source.

Advantageously, the configurations described above allow a high powered accelerators to be powered by low voltage power source, which allows an overall size of the system to be drastically reduced as compared to conventional approaches of powering the same accelerators. In certain embodiments, the relative sizes of the above described components are as follows: a multi-beam klystron having with 16 individual klystrons is about 40 cm×40 cm×40 cm; the RF phase array 16×16 distribution system shown in FIG. 13A is about 25 cm×25 cm×25 cm; and the pulse compressor is about 15 cm×15 cm×15 cm. These components and configuration described above allows the linear accelerator to be powered with about 70 MW of power (pulsed) as compared to conventional RF systems for linear accelerators that require about 200 MW of RF power pulsed to operate without the RF pulse compressor. The present system utilizes 16 multi-beam klystrons each up to 5 MW and uses the pulse compressor to increase the peak power. The 16×16 RF phase array distribution system shown in FIG. 11A can power 16 linear accelerators. In one aspect, providing an RF distribution system having N (input)×N (output) allows N linear accelerators to be powered by power sources operated at considerably reduced voltages, which in turn allows the overall system is drastically reduced, so as to allow the system to fit into a standard treatment room. For example, when providing 70 MW to each accelerator by use of the multi-beam klystron, pulse compressor and phase array configuration described above, each of the multi-klystrons devices may require only a 60 kV voltage modulator, which has a size of about 15 cm×25 cm×40 cm. In contrast, to provide 70 MW with a conventional power source 200, a 400 kV modulator 70 would be required, which has a size of about 5 m×2 m×2 m. To illustrate the considerable differences in size in this modulators and components, a rough approximation of these relative sizes are shown in FIG. 14A.

Figure 14B:
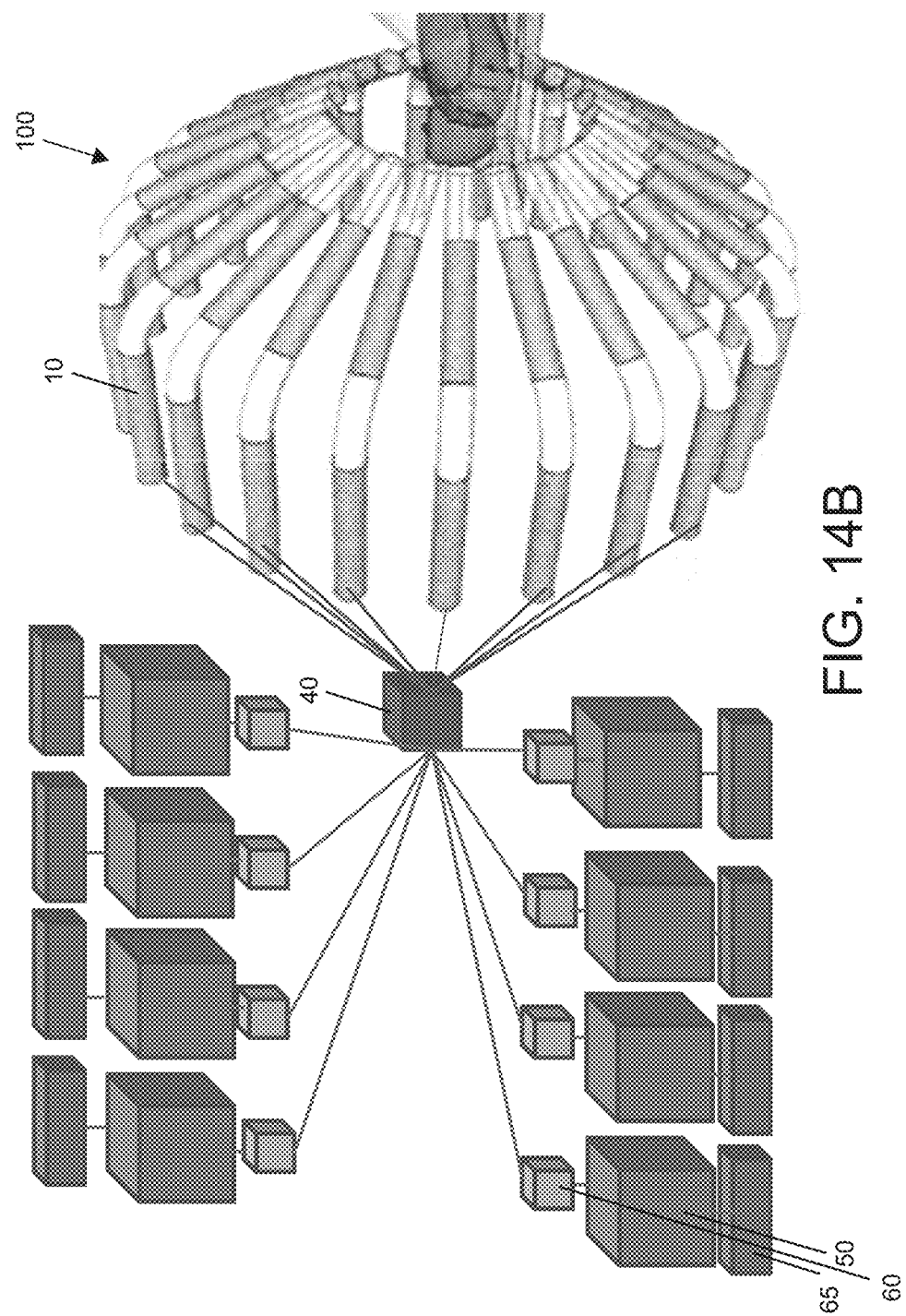
FIG. 14B illustrates a schematic of the components of an example RF power distribution system used to power an array of accelerators of a treatment system in accordance with aspects of the invention.
Figure 14C:
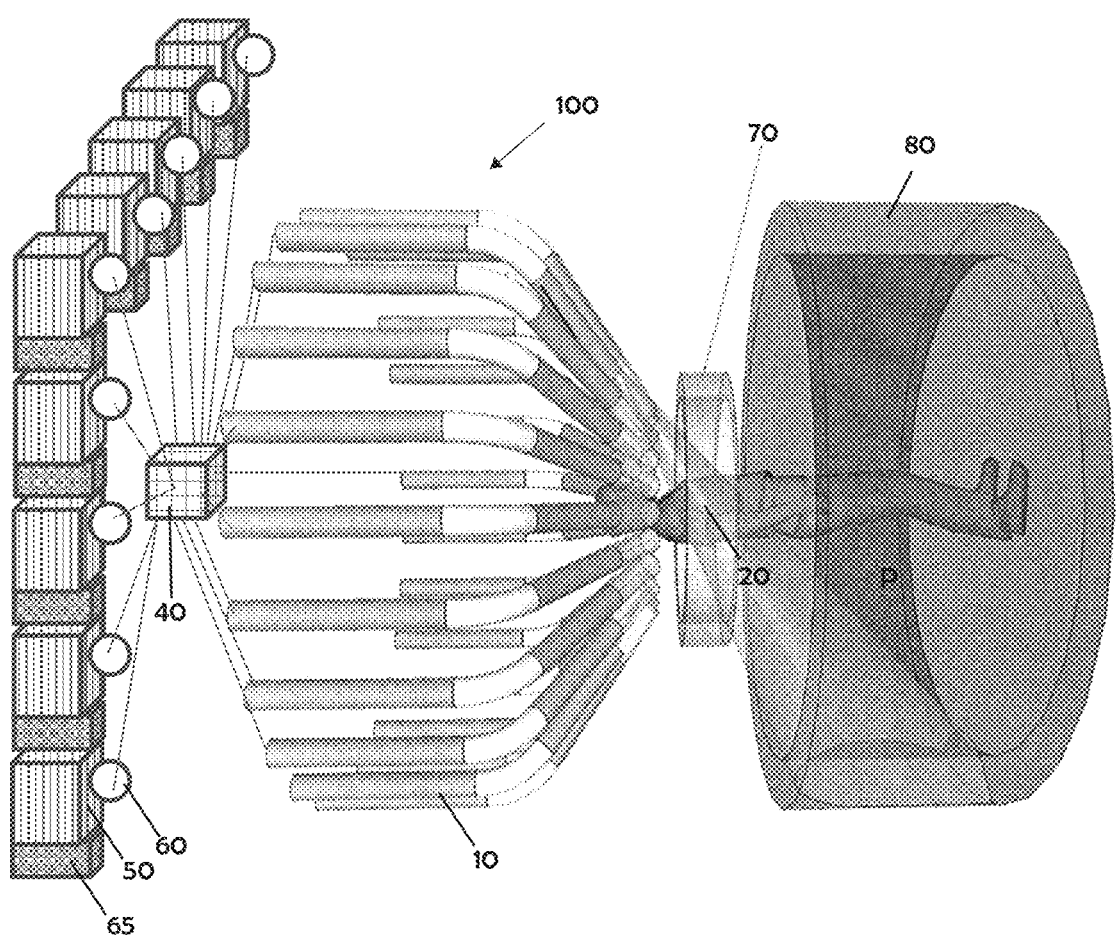
FIG. 14C illustrates an example layout of a treatment system utilizing an array of accelerators and an RF power distribution system in a configuration suited for a standard treatment room, in accordance with aspects of the invention.

FIG. 14B illustrates how the above described components would be connected (for clarity, only 8 linacs are shown connected to the RF power distribution system). FIG. 14C illustrates how such a system having an array of 25 accelerators powered by an array of multi-beam klystron devices coupled through an RF phase array 40. The array of multi-beam klystrons devices may be mounted along a wall. In this example, the array includes a 5×5 array of multi-beam klystrons devices 50 (only top and side row are shown for clarity), each powered by a 60 kV voltage modulator 65 and having a pulse compressor 60 between the RF output and the RF phase array so as to provide the required 70 MW peak power (pulsed) to a select accelerator 10 of the array of accelerators 100. This configuration also allows for positioning of an imaging system 70, such as a full CT ring and a beam dump 80 to absorb any remaining radiation after the treatment beam passes through the target tissue 20 of the patient.

In one aspect, the above described system overcomes drawbacks of conventional treatment systems utilizing linear accelerators. When designing for high-gradient, high efficiency, compact accelerator systems, it is desirable to design and build accelerator structures with the highest possible shunt impedances which allows us to get the highest accelerating gradients for the same amount of RF power and further to make the high power RF sources that are needed as small as possible. In certain applications, RF peak powers in the range of ~100 MW are needed in order to accelerate the beam to the required energy in the ~1 m structures. Conventional RF source technology require very large and very high voltage systems to generate this amount of power, typically room sized and using 400 kV voltages. For many uses the size and high voltage needed for the Rf sources are prohibitive obstacles to the design needs.

The approach described herein is a significant departure from conventional systems and represents a new direction in designing high shunt impedance structures and high power RF sources. For the RF sources, high parallel systems of small klystrons and distribution systems to sum the output powers provide the required RF power needed to drive the high gradient accelerators. In addition, by utilizing individual klystrons having periodic permanent magnets for focusing (instead of solenoid electromagnet) and a depressed collector technology, the efficiency of producing RF power can be drastically improved. Although the individual klystrons have an output power of a few hundred kW, packaging these klystrons (e.g. 16) together and this multi-beam/multi-klystron system can generate multi-MW of RF power. The output of each multi-beam klystron is then fed into a RF pulse compressor to further increase the RF output power (at the expense of RF pulse length). The resulting RF distribution system sums the output of many multi-beam klystrons into a single output, thereby allowing generation of RF power in the ~100 MW range. Furthermore this device has N(inputs)×N(output) and by phasing the N(inputs) we can direct the summed RF power into any of the outputs, which allows multiple linacs to be powered with the same RF source (albeit with correspondingly reduced repetition rate in each linac).

By summing the output of many klystrons, the voltage required to drive each individual klystron is much smaller (e.g. 60 kV instead of 400 kV) such that the modulators required to provide these voltages are much smaller, simpler and cheaper to manufacture. In addition our approach allows us to design both accelerators and RF sources at any frequency and the structures and RF source so generated can be perfectly matched. Another advantages is that this RF power distribution system allows the RF power to be alternated rapidly between multiple linacs of an array of accelerators, so as to retain the advantages of lower operating voltages and reduced size, while still providing a radiation treatment sufficiently rapid to deliver an entire treatment dose in less than 10 seconds, typically less than a few seconds, preferably in one second or less so as to effectively freeze physiologic motion.

C. General

Numerous specific details are set forth herein to provide a thorough understanding of the claimed subject matter. However, those skilled in the art will understand that the claimed subject matter may be practiced without these specific details. In other instances, methods, apparatuses or systems that would be known by one of ordinary skill have not been described in detail so as not to obscure subject matter that may be claimed. Generally, the items depicted in the figures are not drawn to scale, except where indicated otherwise. Where objects are drawn to scale, it is understood that the embodiments are not limited to the size depicted. The sizes of various items have been depicted in order to illustrate the advantages of the present invention in allowing a substantially more compact system than conventional approaches would allow, such that a treatments system in accordance with aspects of the present invention are feasible to construct and operate.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

What is claimed is:

1. A power distribution system for powering multiple particle accelerators, the system comprising:
    a plurality of radio frequency (RF) power sources;
    a plurality of accelerating structures;
    an RF phase array coupling the plurality of RF power sources with the plurality of accelerating structures; and
    a programmable controller operatively coupled with the RF phase array and configured to control a phase and an amplitude of the RF phase array such that a total RF energy from the plurality of RF power sources is directed to a single select accelerating structure of the plurality through source phasing, the single select accelerating structure comprising any of the plurality of accelerating structures.

2. The power distribution system of claim 1, wherein the controller is configured to rapidly adjust the source phasing of the RF array so as to direct the total RF power from the plurality of RF power sources between multiple accelerating structures of the plurality in rapid succession.

3. The power distribution system of claim 1, wherein the controller is configured to adjust the source phasing of the RF array sufficiently rapid so as to direct an entire treatment dosage to a targeted tissue of a patient from multiple accelerating structures of the plurality in less than 10 seconds.

4. The power distribution system of claim 1, wherein each of the plurality of RF power sources provides less power than that required to operate any single accelerating structure of the plurality.

5. The power distribution system of claim 1, wherein each of the plurality of RF power sources is an amplifier type source.

6. The power distribution system of claim 5, wherein each of the plurality of RF power sources is a multi-klystron device, wherein each multi-klystron device is overmolded.

7. The power distribution system of claim 1, wherein each of the plurality of RF power sources is phase locked oscillator.

8. The power distribution system of claim 7, wherein each of the plurality of RF power sources is an externally phase locked magnetron.

9. The power distribution system of claim 1, wherein the plurality of RF power sources comprise linear devices and/or cross field devices.

10. The power distribution system of claim 1, wherein the system is configured such that a plurality of inputs of the plurality of power sources are fed into a passive microwave network, each input of the plurality corresponding to a power source of the plurality.

11. The power distribution system of claim 10, wherein the network comprises a scattering matrix representation that isolates the plurality of inputs from each other.

12. The power distribution system of claim 10, wherein the plurality of power sources comprises N power sources, wherein the network is of a symmetrical design structure such that a plurality of outputs of the plurality of power sources are isolated from each other.

13. The power distribution system of claim 12, wherein the system is configured such a coupling between the respective inputs and outputs of the plurality sources is equal so as to have an amplitude of $1/N^{1/2}$.

14. The power distribution system of claim 1, wherein each of the plurality of power sources operates at 100 kV or less.

15. The power distribution system of claim 14, wherein the total RF power provided by the plurality of RF power sources is 50 MW or greater.

16. A multi-beam system for producing high energy treatment beams using a low voltage power source, the system comprising:
a plurality of klystrons sealed within a common vacuum envelope;
an input combiner extending between each of the plurality of klystrons that defines a buncher cavity for each of the plurality of klystrons; and
an output combiner extending between each of the plurality of klystrons that defines a catcher cavity for each of the plurality of klystrons.

17. The multi-beam system of claim 16, wherein each klystron comprises a drift tube extending between the input combiner and the output combiner.

18. The multi-beam system of claim 17, wherein each klystron include multiple cavities within the drift tube to enhance bunching.

19. The multi-beam system of claim 16, wherein the output combiner has a common cavity such that the catcher cavity of each klystron is in communication with each other, thereby allowing combining of the beams of each klystron and output of the combined beam though a single output.

20. The multi-beam system of claim 19, wherein the klystrons are arranged in a linear array or rectangular array.

21. A method of powering a device comprising:
operating a multi-beam device comprising a plurality of klystrons sealed within a common vacuum envelope, an input combiner extending between each of the plurality of klystrons that defines a buncher cavity for each of the plurality of klystrons, and an output combiner extending between each of the plurality of klystrons that defines a catcher cavity for each of the plurality of klystrons; and
controlling the multi-beam device so as to direct the power output from the plurality of klystrons to the output combiner thereby providing a power output for powering the device, wherein the power output is greater than a power output of any individual klystron of the multi-beam device.

22. A method of powering multiple particle accelerators with a distribution system, the method comprising:
operating a power distribution system comprising a plurality RF power sources and an RF phase array coupling the plurality of RF power sources to a plurality of accelerating structures; and
selecting a single accelerating structure from the plurality of accelerating structures, the single select accelerating structure comprising any of the plurality of accelerating structures; and
controlling the power distribution system, with a controller, to control a phase and an amplitude of the RF phase array so that a total RF energy from the plurality of RF power sources is directed to the single select accelerating structure of the plurality through source phasing.

23. The method of claim 22, wherein each of the plurality of RF power sources operates at 100 kV or less and the total RF power provided by the plurality of RF power sources is 50 MW or greater.

* * * * *

UNITED STATES PATENT AND TRADEMARK OFFICE
CERTIFICATE OF CORRECTION

| | |
|---|---|
| PATENT NO. | : 10,485,991 B2 |
| APPLICATION NO. | : 15/068268 |
| DATED | : November 26, 2019 |
| INVENTOR(S) | : Sami G. Tantawi et al. |

It is certified that error appears in the above-identified patent and that said Letters Patent is hereby corrected as shown below:

In the Specification

Column 1, Line 23 add:
STATEMENT OF GOVERNMENT SPONSORED SUPPORT
This invention was made with Government support under contract DE-AC02-76SF00515 awarded by the Department of Energy. The Government has certain rights in the invention.

Signed and Sealed this
Seventh Day of May, 2024

Katherine Kelly Vidal
*Director of the United States Patent and Trademark Office*